(12) United States Patent
Pippin et al.

(10) Patent No.: US 12,121,697 B2
(45) Date of Patent: Oct. 22, 2024

(54) SYRINGE PUMP WITH SYRINGE POSITION GUIDING FEATURES AND OCCLUSION DETECTION

(71) Applicants: BAXTER INTERNATIONAL INC., Deerfield, IL (US); BAXTER HEALTHCARE SA, Glattpark (CH)

(72) Inventors: Steven S. Pippin, Libertyville, IL (US); Erica Mae Delisle, Chicago, IL (US); Bhagyesh Kishore Bhandar, Mundelein, IL (US); Aaron M. Hexamer, Grayslake, IL (US); Jiri Slaby, Buffalo Grove, IL (US); Peter M. Bojan, Grayslake, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 173 days.

(21) Appl. No.: 16/413,057

(22) Filed: May 15, 2019

(65) Prior Publication Data
US 2019/0351132 A1    Nov. 21, 2019

Related U.S. Application Data

(60) Provisional application No. 62/671,716, filed on May 15, 2018.

(51) Int. Cl.
*A61M 5/142* (2006.01)
*A61M 5/145* (2006.01)
*A61M 5/168* (2006.01)

(52) U.S. Cl.
CPC .... *A61M 5/14236* (2013.01); *A61M 5/14546* (2013.01); *A61M 5/16831* (2013.01);
(Continued)

(58) Field of Classification Search
CPC .......... A61M 5/14326; A61M 5/14546; A61M 5/16831; A61M 2005/14506;
(Continued)

(56) References Cited

U.S. PATENT DOCUMENTS 5,254,096 A * 10/1993 Rondelet ............. A61M 5/1456
604/152
9,289,552 B2 * 3/2016 Gerlach .............. A61M 5/1456
(Continued)

FOREIGN PATENT DOCUMENTS

CN   1490060 A    4/2004
EP   1279410 A1 *  1/2003   .......... A61M 5/1458
(Continued)

OTHER PUBLICATIONS

Written Opinion of the International Searching Authority mailed Oct. 16, 2019 in corresponding PCT Application No. PCT/US2019/032443.

(Continued)

*Primary Examiner* — Chelsea E Stinson
*Assistant Examiner* — Robert F Allen
(74) *Attorney, Agent, or Firm* — K&L Gates LLP

(57) ABSTRACT

A syringe pump including a housing with a syringe accepting region, a syringe holding system configured to hold a syringe in the syringe accepting region, a drive mechanism, and a drive head operatively coupled to the drive mechanism. The drive head is configured to engage a piston of a syringe held by the syringe holding system.

15 Claims, 15 Drawing Sheets

(52) U.S. Cl.
CPC ............. *A61M 2005/14506* (2013.01); *A61M 2005/14533* (2013.01); *A61M 5/1456* (2013.01); *A61M 2005/14573* (2013.01); *A61M 2005/16868* (2013.01); *A61M 2205/332* (2013.01); *A61M 2205/3331* (2013.01); *A61M 2205/502* (2013.01); *A61M 2205/6054* (2013.01)

(58) Field of Classification Search
CPC ......... A61M 2005/14533; A61M 2005/16868; A61M 2205/332; A61M 2205/3331; A61M 2205/502; A61M 2205/6054; A61M 5/1452; A61M 5/1458; A61M 5/14566; A61M 5/172; A61M 5/142; A61M 5/14236; A61M 2005/16863; A61M 5/1456; A61M 2005/14573; A61B 17/1707; F16D 2500/10475; F16K 31/001; F16K 31/002; F16K 31/003; F16K 31/004; F16K 31/005; F16K 31/006; F16K 31/007; F16K 31/02; F16K 31/025; F16K 31/04; F16K 31/041; F16K 31/042; F16K 31/043; F16K 31/045; F16K 31/046; F16K 31/047; F16K 31/048; F16K 31/05; F16K 31/055; F16K 31/06; F16K 31/0603; F16K 31/0606; F16K 31/061; F16K 31/0613; F16K 31/0617; F16K 31/062; F16K 31/0624; F16K 31/0627; F16K 31/063; F16K 31/0631; F16K 31/0634; F16K 31/0637; F16K 31/0641; F16K 31/0644; F16K 31/0648; F16K 31/0655; F16K 31/0658; F16K 31/0662; F16K 31/0665; F16K 31/0668; F16K 31/0672; F16K 31/0675; F16K 31/0679; F16K 31/0682; F16K 31/0686; F16K 31/0689; F16K 31/0693; F16K 31/0696; F16K 31/08; F16K 31/082; F16K 31/084; F16K 31/086; F16K 31/088; F16K 31/0651; F16K 31/008; G16H 20/17
See application file for complete search history.

(56) References Cited

U.S. PATENT DOCUMENTS

| | | | |
|---|---|---|---|
| 2002/0183616 A1* | 12/2002 | Toews | A61M 5/007 128/920 |
| 2004/0057855 A1* | 3/2004 | Gerlach | A61M 5/142 417/469 |
| 2006/0184123 A1 | 8/2006 | Gillespie, Jr. et al. | |
| 2011/0105955 A1* | 5/2011 | Yudovsky | A61M 5/1723 600/595 |
| 2014/0188076 A1* | 7/2014 | Kamen | F04B 1/26 604/154 |
| 2016/0030663 A1 | 2/2016 | Adaniya et al. | |
| 2017/0258985 A1 | 9/2017 | Adams | |
| 2018/0347722 A1* | 12/2018 | Bähr | F16K 31/082 |

FOREIGN PATENT DOCUMENTS

| | | |
|---|---|---|
| EP | 1723978 A2 | 11/2006 |
| JP | 2004-024874 A | 1/2004 |
| JP | 2016-508045 A | 3/2016 |
| KR | 20180006657 A | 1/2018 |
| WO | WO 2005004952 A1 | 1/2005 |
| WO | WO 2014100658 A1 | 6/2014 |

OTHER PUBLICATIONS

International Search Report mailed Oct. 16, 2019 in corresponding PCT Application No. PCT/US2019/032443.
First Office Action issued by Chinese Patent Office on Apr. 24, 2022. Chinese Patent Application Invention No. 201980031432.X, Received: May 6, 2022.
Japanese Notice of Reasons for Rejection for corresponding Japanese Patent Application No. 2020-558883, mailed Mar. 28, 2023.
Notice of Reasons for Rejection from corresponding Japanese Patent Application No. 2020-558883, mailed Oct. 3, 2023. English Translation only. 2 pages.
Canadian Office Action from corresponding Canadian Patent Application No. 3,100,209, dated Nov. 2, 2023. 4 pages.
Notice of Preliminary Rejection from Korean Patent Application No. 10-2020-7035547, mailed May 22, 2024 (English Translation included). 20 pages.
Mexican Office Action from corresponding Mexican Patent Application No. MX/a/2020/012271, mailed Jan. 31, 2024. 7 pages.

* cited by examiner

SYRINGE PUMP WITH SYRINGE POSITION GUIDING FEATURES AND OCCLUSION DETECTION

RELATED APPLICATIONS

This application claims the benefit of and priority to U.S. Provisional Patent Application No. 62/671,716 filed May 15, 2018, entitled "SYRINGE PUMP," which is incorporated herein by reference in its entirety.

BACKGROUND

Generally, medical patients sometimes require precise delivery of either continuous medication or medication at set periodic intervals. Medical pumps have been developed to provide controlled drug infusion wherein the drug can be administered at a precise rate that keeps the drug concentration within a therapeutic margin and out of an unnecessary or possibly toxic range. Basically, the medical pumps provide appropriate drug delivery to the patient at a controllable rate, which does not require frequent attention.

Medical pumps may facilitate administration of intravenous therapy to patients both in and outside of a clinical setting. Outside a clinical setting, doctors have found that in many instances patients can return to substantially normal lives, provided that they receive periodic or continuous intravenous administration of medication. Among the types of therapies requiring this kind of administration are antibiotic therapy, chemotherapy, pain control therapy, nutritional therapy, and several other types known by those skilled in the art. In many cases, patients receive multiple daily therapies. Certain medical conditions require infusions of drugs in solution over relatively short periods such as from 30 minutes to two hours. These conditions and others have combined to promote the development of increasingly lightweight, portable or ambulatory infusion pumps that can be worn by a patient and are capable of administering a continuous supply of medication at a desired rate, or provide several doses of medication at scheduled intervals.

Additional problems have also been experienced with infusion pumps. For example, certain sensing systems that detect whether an occlusion is present in an infusion line have proven to be unreliable or too complex in construction. Certain syringe plunger position detectors and syringe barrel size detectors have also proven to be unreliable. In addition, drive mechanisms for syringe plungers have also proven to be unreliable as certain components become stripped or jammed adversely affecting the mechanism.

SUMMARY

The present invention is generally directed to a syringe pump for delivering a flowable material, such as a fluid medication, to a patient through an infusion line.

Aspects of the subject matter described herein may be useful alone or in combination with one or more other aspects described herein. In an exemplary aspect of the present disclosure, a syringe pump includes a housing with a syringe-accepting region.

In accordance with a second exemplary aspect of the present disclosure, which may be used in combination with any one or more of the preceding aspects, the syringe pump includes a syringe holding system configured to hold a syringe in the syringe-accepting region.

In accordance with a second exemplary aspect of the present disclosure, which may be used in combination with any one or more of the preceding aspects, the syringe pump includes a drive mechanism.

In accordance with a second exemplary aspect of the present disclosure, which may be used in combination with any one or more of the preceding aspects, the syringe pump includes a drive head operatively coupled to the drive mechanism. The drive head may be configured to engage a piston of a syringe held by the syringe holding system.

In accordance with a second exemplary aspect of the present disclosure, which may be used in combination with any one or more of the preceding aspects, the syringe-accepting region includes a concave rear wall having a vertex, where the concave rear wall includes a top portion and a bottom portion that meet to form the vertex.

In accordance with a second exemplary aspect of the present disclosure, which may be used in combination with any one or more of the preceding aspects, the top portion is oriented at a first angle with respect to a vertical plane intersecting the vertex.

In accordance with a second exemplary aspect of the present disclosure, which may be used in combination with any one or more of the preceding aspects, the bottom portion is oriented at a second angle with respect to a vertical plane intersecting the vertex.

In accordance with a second exemplary aspect of the present disclosure, which may be used in combination with any one or more of the preceding aspects, the first angle and the second angle are the same.

In accordance with another exemplary aspect of the present disclosure, which may be used in combination with any one or more of the preceding aspects, the drive head includes first and second plunger hooks disposed on the drive head.

In accordance with another exemplary aspect of the present disclosure, which may be used in combination with any one or more of the preceding aspects, the plunger hooks are configured to grasp onto a plunger thumb flange of a plunger of the syringe. Additionally, the first and second plunger hooks are configured to actuate between an open position and a closed position.

In accordance with another exemplary aspect of the present disclosure, which may be used in combination with any one or more of the preceding aspects, the drive head includes a plunger lever. The plunger lever is adapted to move the plunger hooks between the open position and the closed position. Additionally, the plunger lever is configured for actuation by a user.

In accordance with another exemplary aspect of the present disclosure, which may be used in combination with any one or more of the preceding aspects, the drive mechanism includes a lead screw, a split-nut, a clutch assembly, and a drive rod. The clutch assembly is configured to engage and disengage the split-nut to and from the lead screw.

In accordance with another exemplary aspect of the present disclosure, which may be used in combination with any one or more of the preceding aspects, the clutch assembly includes a magnet configured to increase a holding force of the clutch assembly and prevent ratcheting.

In accordance with another exemplary aspect of the present disclosure, which may be used in combination with any one or more of the preceding aspects, the syringe holding system includes a barrel clamp, a flange plate, and first and second syringe hooks.

In accordance with another exemplary aspect of the present disclosure, which may be used in combination with any one or more of the preceding aspects, the drive mechanism includes an anti-ratcheting magnetic clutch.

In accordance with another exemplary aspect of the present disclosure, which may be used in combination with any one or more of the preceding aspects, the syringe pump further includes an occlusion sensor. The occlusion sensor is configured to determine if an infusion line connected to the syringe barrel is blocked.

In accordance with another exemplary aspect of the present disclosure, which may be used in combination with any one or more of the preceding aspects, the occlusion sensor determines if an infusion line connected to the syringe barrel is blocked by calculating a slope of a force curve, a slope of a pressure curve, a comparison to a baseline force measurement, a comparison to a baseline pressure measurement, or an area under the force curve.

In accordance with another exemplary aspect of the present disclosure, which may be used in combination with any one or more of the preceding aspects, the syringe pump further includes an accelerometer, wherein the accelerometer is configured to detect at least one of an occlusion or whether the syringe pump experienced an external impact.

In accordance with another exemplary aspect of the present disclosure, which may be used in combination with any one or more of the preceding aspects, the syringe pump is positioned in a rack with at least one other infusion pump or syringe pump.

Aspects of the subject matter described herein may be useful alone or in combination with one or more other aspects described herein. In an exemplary aspect of the present disclosure, a syringe positioning system for positioning a plurality of syringes having respective barrels and respective plungers within a syringe pump housing includes a barrel clamp, a flange plate, and first and second plunger hooks. The barrel clamp is adjustable to hold the syringe barrel against the syringe pump housing. The flange plate is configured to secure a syringe barrel flange against the syringe pump housing. Additionally, the plunger hooks are configured to grasp onto a plunger thumb flange of the plunger of the syringe. The first and second plunger hooks are also configured to actuate between an open position and a closed position.

In accordance with another exemplary aspect of the present disclosure, which may be used in combination with any one or more of the preceding aspects, the syringe positioning system is further configured to position a plurality of syringes having different sizes.

In accordance with another exemplary aspect of the present disclosure, which may be used in combination with any one or more of the preceding aspects, the syringe positioning system further includes a position sensor configured to detect a rotation of the syringe barrel clamp.

In accordance with another exemplary aspect of the present disclosure, which may be used in combination with any one or more of the preceding aspects, the barrel clamp includes a proximal end pivotably attached to the housing and a distal end with a barrel engagement surface.

In accordance with another exemplary aspect of the present disclosure, which may be used in combination with any one or more of the preceding aspects, the barrel engagement surface is attached to the barrel clamp via a swivel and is adapted to allow the barrel engagement surface to rotate and contact syringe barrels of at least two different sizes.

In accordance with another exemplary aspect of the present disclosure, which may be used in combination with any one or more of the preceding aspects, the flange plate is configured to secure a syringe barrel flange against the housing.

In accordance with another exemplary aspect of the present disclosure, which may be used in combination with any one or more of the preceding aspects, the flange plate is biased towards the housing.

In accordance with another exemplary aspect of the present disclosure, which may be used in combination with any one or more of the preceding aspects, the flange plate includes a bottom surface configured to contact the syringe barrel flange, and the flange plate has a surface profile that transitions from a flat surface to an angled surface towards the edge of the flange plate.

Aspects of the subject matter described herein may be useful alone or in combination with one or more other aspects described herein. In an exemplary aspect of the present disclosure, a method of detecting an occlusion includes monitoring a pressure measurement. The pressure measurement may be based on an ADC value.

In accordance with another exemplary aspect of the present disclosure, which may be used in combination with any one or more of the preceding aspects, the method includes, during a first interval, recording a baseline pressure measurement.

In accordance with another exemplary aspect of the present disclosure, which may be used in combination with any one or more of the preceding aspects, the method includes, during a second interval, determining whether a respective current pressure measurement exceeds a first difference threshold between the current pressure measurement and the baseline pressure measurement. The first difference threshold may be based on a selected occlusion detection mode.

In accordance with another exemplary aspect of the present disclosure, which may be used in combination with any one or more of the preceding aspects, the method includes, during a third interval, after the first interval and the second interval, recording a new baseline pressure measurement.

In accordance with another exemplary aspect of the present disclosure, which may be used in combination with any one or more of the preceding aspects, the method includes, after determining the new baseline pressure measurement, determining whether a respective current pressure measurement exceeds a second difference threshold between the respective current pressure measurement and the new baseline pressure measurement.

In accordance with another exemplary aspect of the present disclosure, which may be used in combination with any one or more of the preceding aspects, the method includes determining an occlusion exists within a tube of an infusion pump when at least one of the first difference threshold and the second difference threshold is exceeded.

In accordance with another exemplary aspect of the present disclosure, which may be used in combination with any one or more of the preceding aspects, the selected occlusion detection mode includes either a rapid occlusion detection mode or a non-rapid occlusion detection mode. Additionally, the threshold may be lower for the rapid occlusion detection mode than the non-rapid occlusion detection mode.

To the extent that any of these aspects are mutually exclusive, it should be understood that such mutual exclusivity shall not limit in any way the combination of such aspects with any other aspect whether or not such aspect is explicitly recited. Any of these aspects may be claimed, without limitation, as a system, method, apparatus, device, medium, etc.

Therefore, it is a primary object of the invention to provide a syringe pump capable of consistently accommodating syringes of different sizes.

It is another object of the invention to provide a syringe pump capable of detecting proper syringe loading and distinguishing syringe sizes.

It is a further object of the invention to provide a syringe pump with an anti-ratcheting magnetic clutch to reduce wear on a lead screw and split-nut.

It is another object of the invention to provide occlusion detection for a syringe pump.

It is an additional object of the invention to provide drop detection for a syringe pump.

It is a further object of the invention to provide power management for a syringe pump loaded in a rack configuration.

Additional features and advantages of the disclosed syringe pump are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

DETAILED DESCRIPTION OF EXAMPLE EMBODIMENTS

Figure 8:
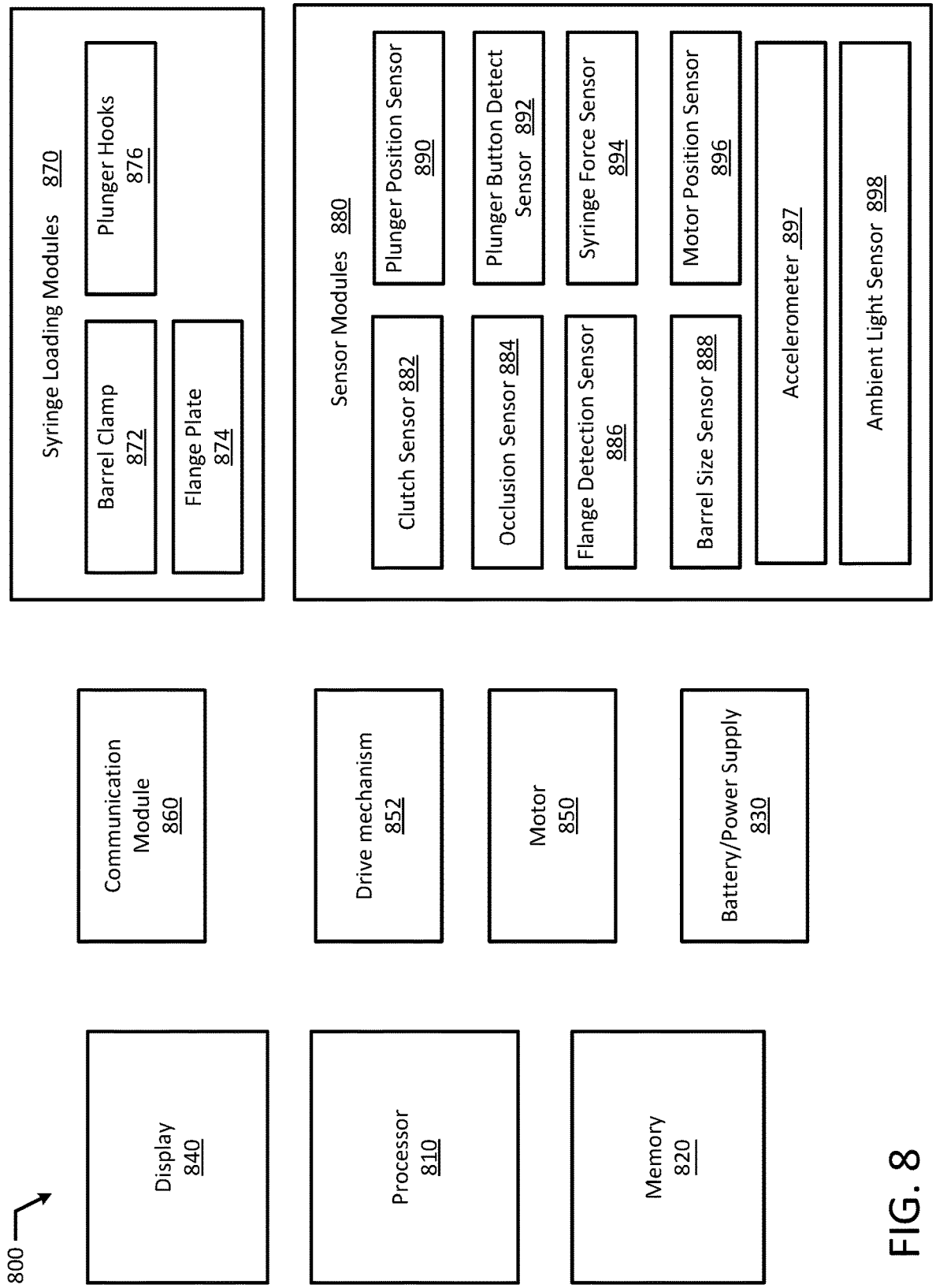
FIG. 8 illustrates a block diagram of an example syringe pump system according to an example embodiment of the present disclosure.
Figure 9A:
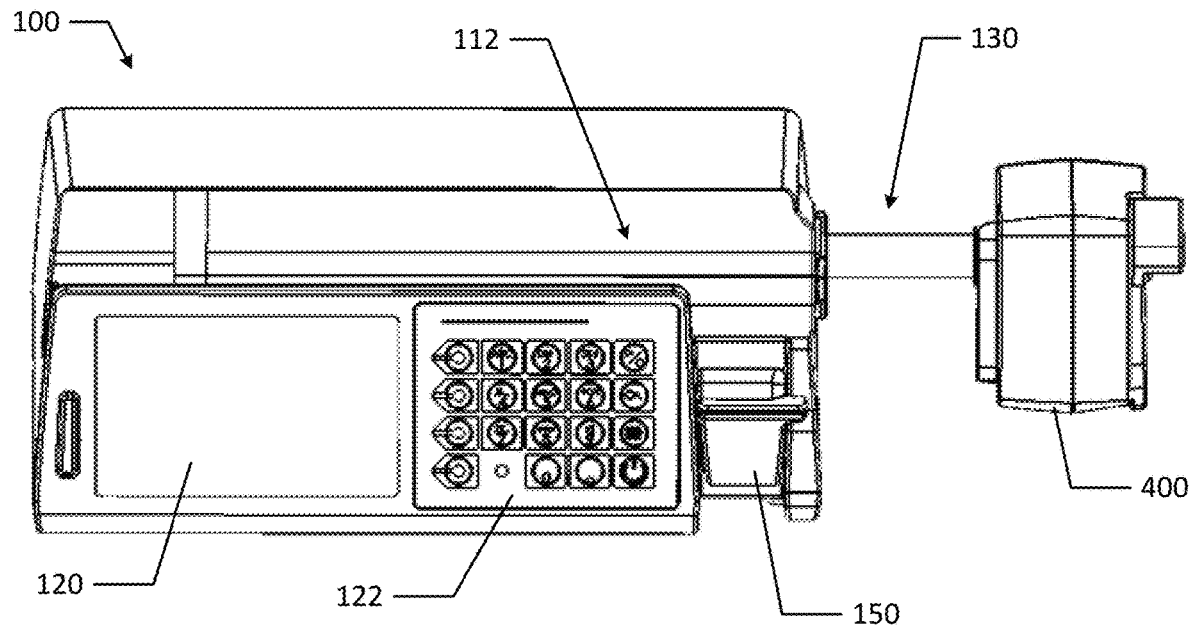
FIGS. 9A, 9B, 9C, and 9D illustrate various perspective views of an example syringe pump according to an example embodiment of the present disclosure.
Figure 9B:
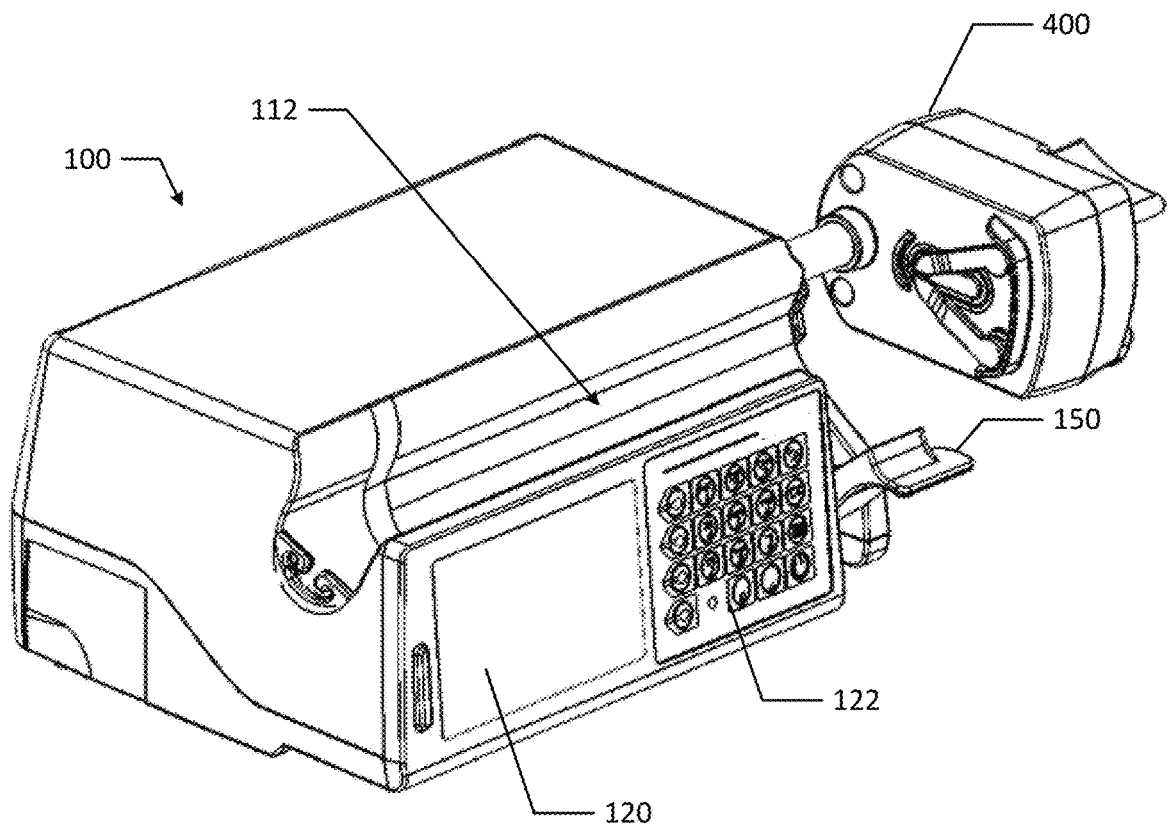
Figure 9C:
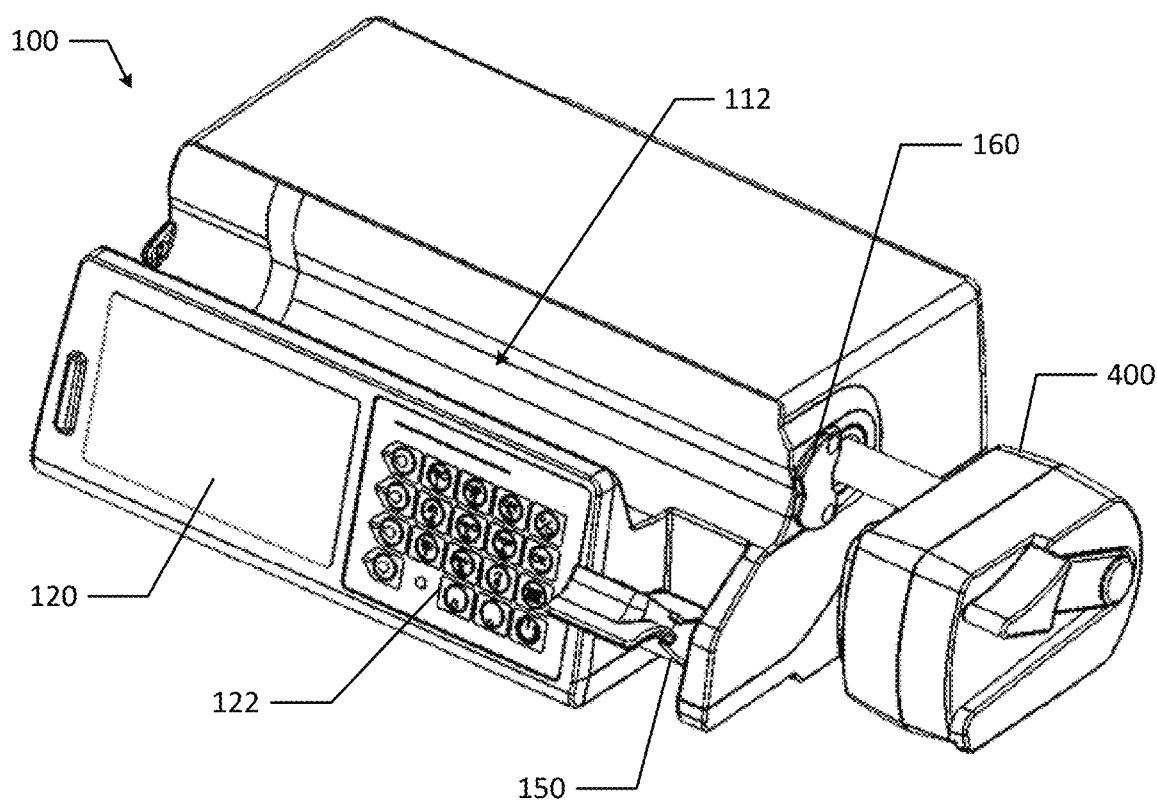
Figure 9D:
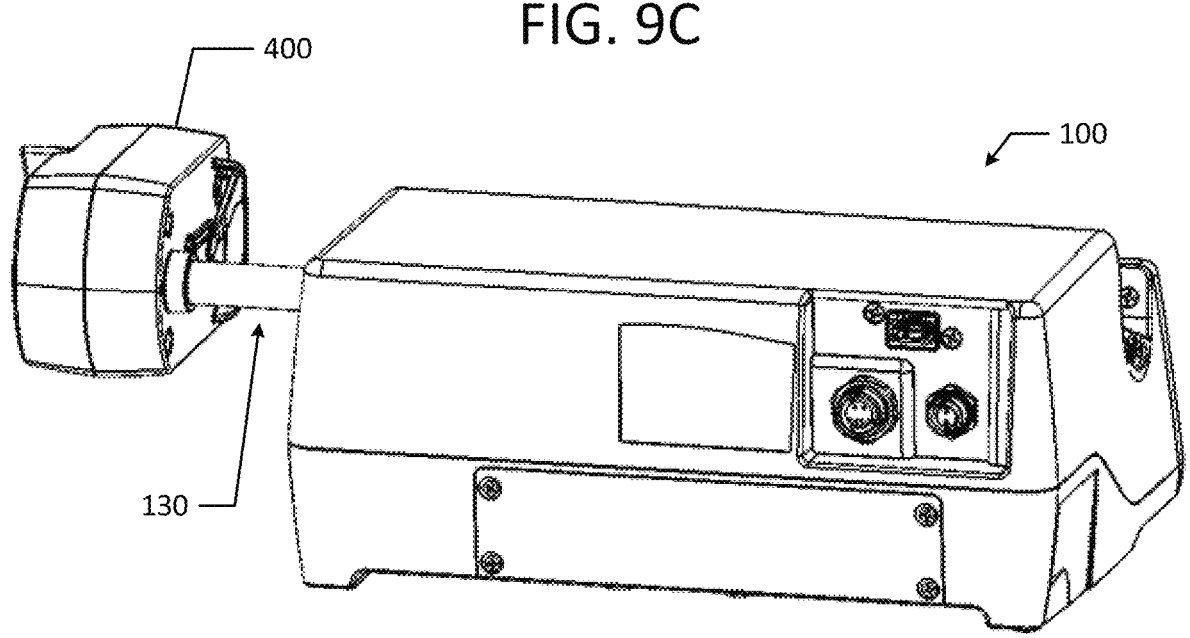

A syringe pump is disclosed. FIG. 8 depicts a high-level component diagram of a syringe pump system 800. The syringe pump system 800 includes a processor 810 in communication with memory 820, which is powered by a battery or power supply 830. The processor 810 communicates with a display 840, a motor 850 and associated drive mechanism 852, and a communication module 860. The pump system 800 may also include syringe-loading modules 870, such as a barrel clamp 872, a flange plate 874 and plunger hooks 876 to engage a syringe plunger. Additionally, the syringe pump system 800 may include various sensor modules 880, such as a clutch sensor 882, an occlusion sensor 884, a flange detection sensor 886, a barrel size sensor 888, a plunger position sensor 890, a plunger button detect sensor 892, a syringe force sensor 894, a motor position sensor 896, an accelerometer 897 and/or an ambient light sensor 898.

In various embodiments, the pump is adapted to supply fluid at various flow rate ranges. Some example non-limiting infusion rates include 0.01 to approximately 30 mL/hr. for a 1 mL syringe; 0.01 to approximately 105 mL/hr. for a 3 mL syringe; 0.03 to approximately 210 mL/hr. for a 5 ml syringe; 0.05 to approximately 315 mL/hr. for a 10 ml syringe; 0.1 to approximately 525 mL/hr. for a 20 ml syringe; 0.1 to approximately 680 mL/hr. for a 30 mL syringe; and 0.1 to approximately 1200 mL/hr. for a 50 or 60 mL syringe.

The Pump Assembly

Figure 1A:
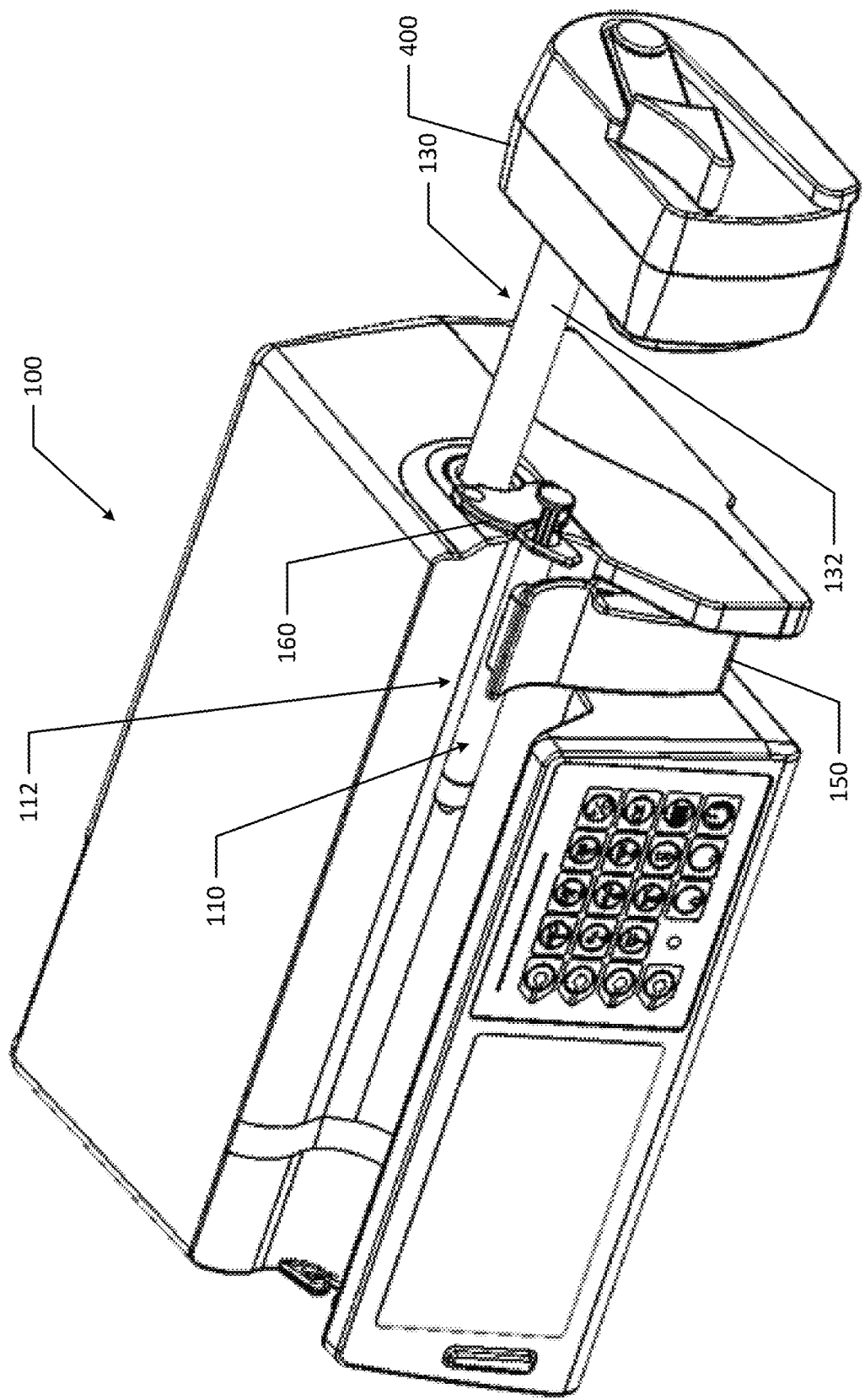
FIGS. 1A and 1B are isometric views of a syringe pump according to an example embodiment of the present disclosure.
Figure 1B:
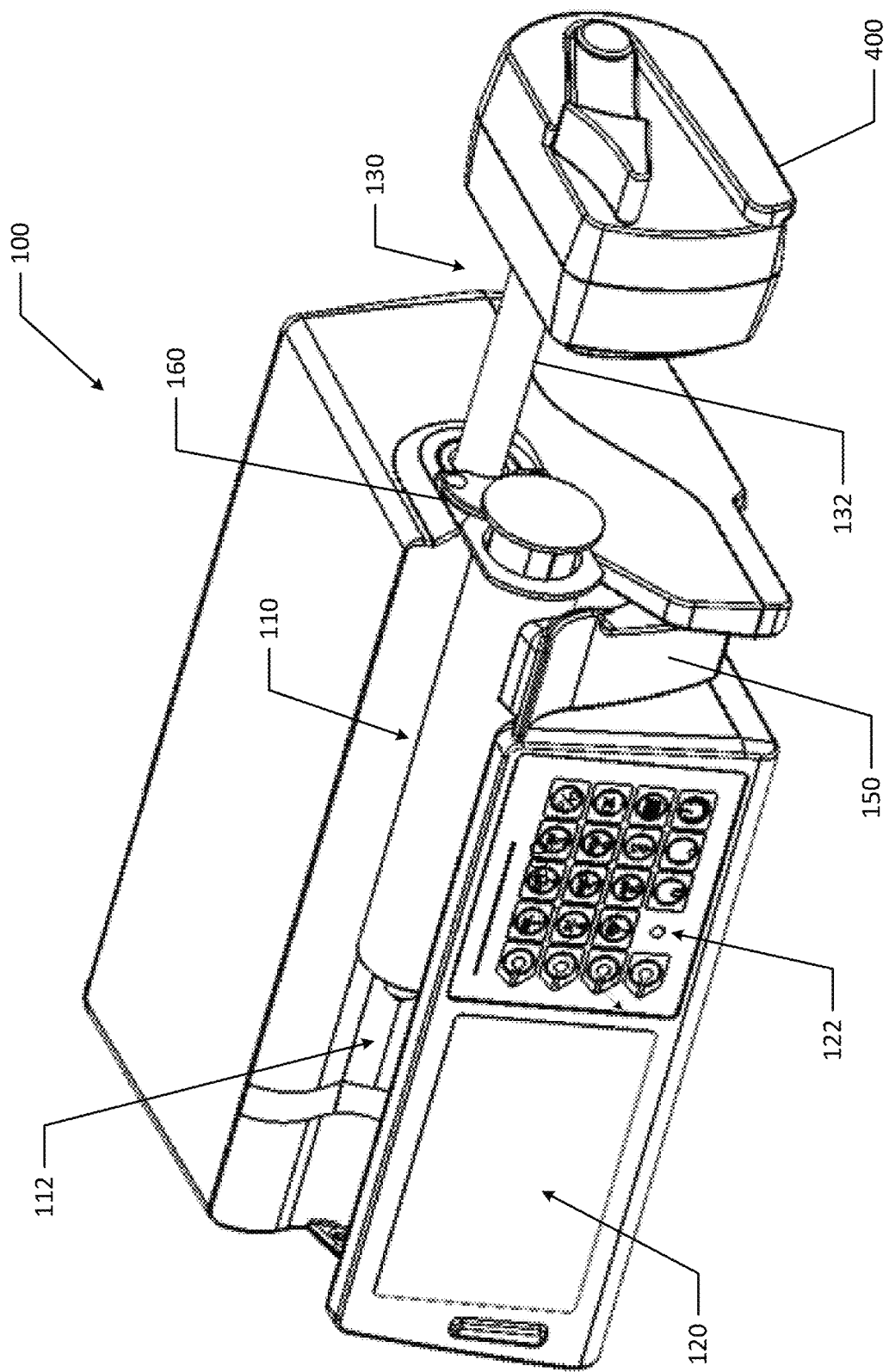

Referring to FIGS. 1A and 1B, an infusion pump or syringe pump 100 generally includes a housing that supports a syringe assembly 110, a user interface or display 120, a keypad 122, a power supply, and a drive mechanism 130. The drive mechanism 130 includes a lead screw, split-nut, and a drive rod 132. As discussed in more detail below, the syringe pump may also include a syringe sensor system. Other examples of syringe pumps include an infusion pump described in U.S. Pat. No. 7,608,060 the entirety of which is incorporated herein by reference. The above example is non-limiting and the concepts disclosed herein could apply to other medical devices and/or syringe pumps such as an infusion pump.

The housing houses various components of the pump including the user interface or display 120 that includes a display screen and a keypad 122. At a bottom, front portion of the housing, a container compartment or syringe compartment 112 is defined that accommodates the syringe assembly 110. The housing can be made from a variety of materials including various types of plastics and metals.

The user interface 120 generally includes a display screen. The display screen may act as a touch screen for data to be inputted into the pump by a user. The display 120 and the keypad 122 are used to program the infusion pump 100, and more specifically, a processor in the pump to set the fluid delivery amount, etc., which is later communicated to the drive mechanism. The pump 100 and user interface or display 120 may utilize additional identification features regarding the medication delivered by the pump. For example, the pump 100 may be equipped with an RFID (radio frequency identification) reader or other identification reader that cooperates with an RFID tag or other identifier attached to a syringe barrel. The RFID tag can store significant information including, but not limited to, the type of medication, amount, concentration, as well as pumping parameters and instructions for the medication.

The display screen may be equipped with a pad about the outer periphery of the screen. The pad is a shock absorbent member made preferably of an elastomeric material. In one preferred embodiment, the pad is made from polyurethane. The pad absorbs forces generated if the pump is jostled, bumped or dropped, and minimizes the effect such occurrences have on the display screen.

The pump 100 includes a power supply that can take many different forms. In one preferred embodiment, the power supply may be in the form of a rechargeable battery unit. Additionally, the pump may be powered from an AC power supply. The AC power supply assembly has a power cord and an associated terminal that plugs into the housing. The AC power supply assembly has a plug that can be inserted into a standard electrical outlet to recharge the rechargeable battery when necessary. The AC power can also be supplied through the assembly to power the pump.

Generally, the syringe compartment 112 is dimensioned to receive and support the syringe assembly 110. The syringe assembly 110 generally includes a syringe barrel and a syringe plunger. The syringe barrel contains medication and slidably receives the syringe plunger. The syringe plunger is driven by the drive mechanism to force medication from the syringe barrel through a tube (not shown) and to a patient. The tube would have one end connected to an end of the syringe barrel and another end adapted to be connected to a patient.

FIGS. 9A to 9D illustrate various other perspective views of an example syringe pump 100. Similar to FIGS. 1A and 1B, syringe pump 100 illustrated in FIGS. 9A to 9D generally includes a user interface or display 120, a keypad 122, a power supply, a drive mechanism 130, and a drive head 400.

The housing houses various components of the pump including the user interface or display 120 that includes a display screen and a keypad 122. At a bottom, front portion of the housing, a container compartment or syringe compartment 112 is defined that accommodates the syringe assembly.

Syringe Barrel Position—Syringe Wall

Figure 2:
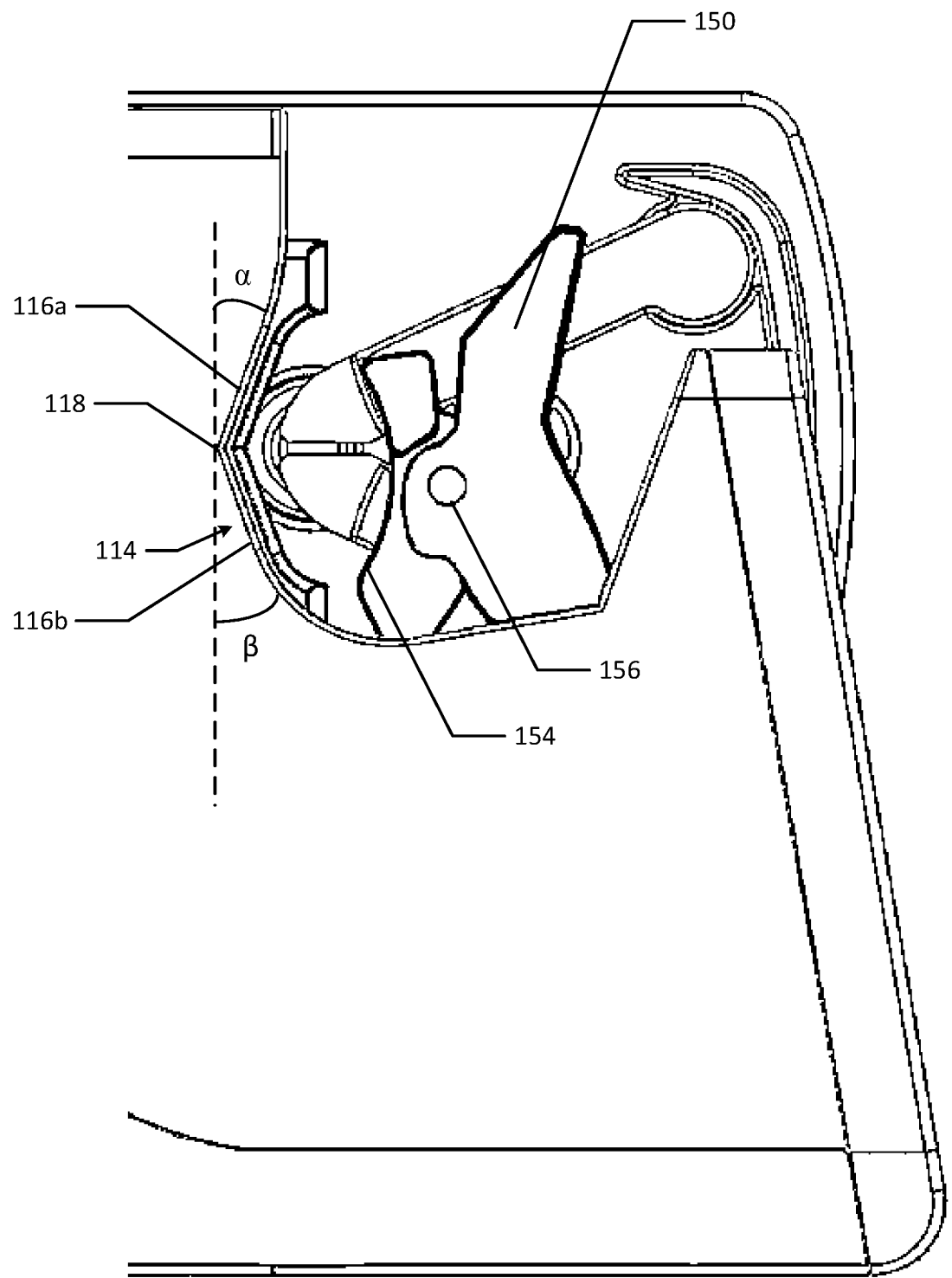
FIG. 2 is a partial view of a syringe compartment of a syringe pump according to an example embodiment of the present disclosure.

The syringe compartment 112 has a rear wall 114 that is generally concave to receive the syringe barrel of the syringe assembly (as illustrated in FIG. 2). The syringe barrel of the syringe assembly and rear wall 114 are generally in confronting relation. The rear wall 114 may include a top portion 116a and a bottom portion 116b that meet at a vertex 118. The top portion 116a has a wall angle ($\alpha$) with respect to a vertical plane that intersects the vertex 118. Similarly, the bottom portion 116b has a wall angle ($\beta$) with respect to a vertical plane that intersects the vertex 118, for example 20 degrees, which improves consistent barrel position and assists with securing the syringe. The wall angles ($\alpha$, $\beta$) may be the same or different. For example, the wall angle ($\alpha$) for the top portion 116a may be larger than the wall angle ($\beta$). In another example, the wall angle ($\alpha$) for the top portion 116a may be smaller than the wall angle ($\beta$) for the bottom portion 116b. The larger the wall angle ($\alpha$, $\beta$), the larger distance between the centers of the smallest and largest syringes loaded in the syringe pump 100. For example, a flat rear wall 114 would allow the center of a syringe barrel to sit at the syringe barrel radius from the rear wall 114. If the rear wall is convex, the center of a syringe barrel is moved further and further away from the vertex 118 as the syringe barrel diameter increases. For example, a small diameter syringe can be positioned close to the vertex 118, but a large diameter syringe may contact the top and bottom portions 116a, b of the rear wall 114 at a greater distance from the vertex 118. Even though larger wall angles ($\alpha$, $\beta$) create larger distances between the centers of different syringes loaded in the syringe pump 100, larger wall angles ($\alpha$, $\beta$) advantageously help mitigate syringe misloading by providing a deeper notch to guide the syringe towards the vertex 118 of the rear wall 114.

Syringe Barrel Clamp

A syringe barrel clamp 150 is movably mounted in the compartment. The clamp 150 has a concave inner surface 154 that faces the rear wall 114 and that fits over the syringe barrel. The clamp 150 is pivotable to move the clamp 150 towards and away from the rear wall 114. Additionally, the clamp 150 is pivotable to accommodate different sized syringe barrels. The syringe barrel clamp 150 is configured to pivot towards the rear wall 114 or a home closed position as well as away from the rear wall 114 to an open position. For example, barrel clamp 150 may be spring biased to pivot about pivot 152 (illustrated in FIG. 3A) to find a home closed position or consistent position such that the clamp 150 is adapted to distinguish different syringes as well as consistently place barrels of the same size. The spring bias towards the home closed position also ensures that a syringe loaded into pump 100 does not come loose if the pump 100 is accidentally bumped. As the barrel clamp 150 is opened, after a certain point in rotation, the clamp is biased towards an open position instead of the home closed position. For example, as a user is opening barrel clamp 150, after a certain degree of rotation, the barrel clamp 150 becomes biased to the open position, which advantageously facilitates ease of syringe loading (e.g., one handed syringe loading). As the user begins to close the barrel clamp 150, the clamp rotates beyond the open position bias and again becomes biased towards the home closed position.

As illustrated in FIG. 2, the inner surface 154 of barrel clamp 150 is included on a swivel 156 to aid in retaining different size syringes. Both swivel 156 and pivot 152 are adapted to consistently locate and position syringes in pump 100. The pivot 152 controls the point about which the entire barrel clamp 150 rotates while the swivel 156 controls the orientation of the barrel-contacting surface of the barrel clamp 150. Pump 100 may be compatible with and support various syringe sizes (e.g., 1 mL, 3 mL, 5 mL, 10 mL, 20 mL, 30 mL, and 50/60 mL syringes) from various syringe manufacturers.

Additionally, as illustrated in FIGS. 1A and 1B, the syringe pump housing may nest the syringe barrel clamp 150 thereby protecting the clamp 150 on each side from accidental bumps or unintentional clamp engagement from either side of the housing.

As discussed in more detail herein, the syringe barrel loading includes barrel size detection means. For example, a rotary potentiometer may be used to detect the size of a syringe barrel. The potentiometer may be geared up 3:1 to obtain appropriate resolution to differentiate between syringe sizes. In another example, a linear potentiometer may be used to detect the size of the syringe barrel.

Syringe Barrel Flange Clamp

The syringe is also held in place on pump 100 by flange plate or barrel flange clamp 160. Flange plate 160 is adapted to secure a syringe by holding the syringe barrel flange against the housing under a compressive force. In an example, the flange plate 160 is spring biased towards the pump housing.

The flange plate 160 includes an angled profile 162 to assist the barrel flange to slide into place. For example, the angled profile 162 allows a barrel flange to be inserted under the outer lip of flange plate 160 and as the barrel flange is moved further towards the pump housing, the angled profile guides the barrel flange in towards the housing and under the flange plate 160 until the force overcomes the spring bias. Once a user overcomes the retention force from the spring bias, the flange plate 160 extends away from the housing to accommodate the width of the barrel flange. The spring bias retains the barrel flange against the housing under a compressive force until the syringe is later removed by a user.

In an example, actuation of the plunger loading lever (illustrated in FIG. 4B) may move the flange plate 160 out away from the pump housing so a user may load a syringe. Other biasing mechanisms or translation mechanisms may be used to move the flange plate 160 towards and away from the pump housing for syringe loading.

Syringe Flippers

Figure 4A:
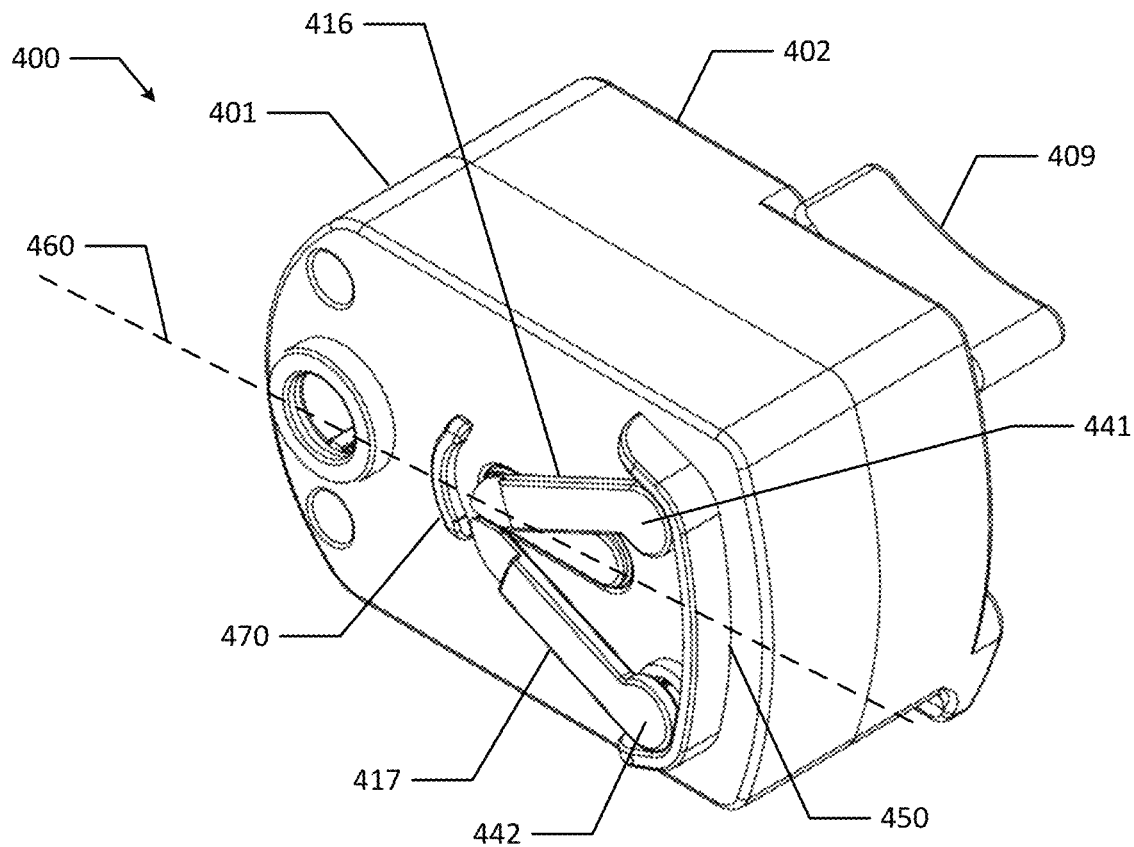
FIGS. 4A and 4B are isometric views of a drive head of a syringe pump according to an example embodiment of the present disclosure.

As illustrated in FIG. 4A, the drive head 400 of the drive mechanism includes two syringe flippers or plunger hooks 416 and 417 on the plunger driver. The size and orientation of the plunger hooks 416, 417 allow full compression of the syringe plunger. The plunger hooks 416, 417 are biased towards the syringe plane 460 about pivots 441 and 442. The pivots 441, 442 positioned on the distal-most side of the drive head 400 away from the pump housing reduce plunger hook interference with the pump to allow full compression of the syringe plunger.

Figure 4B:
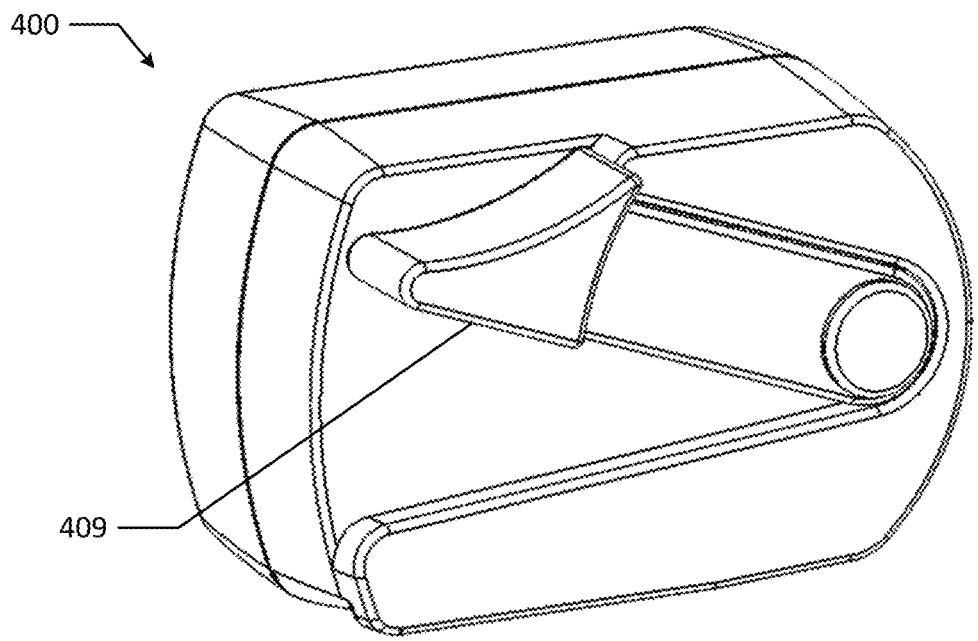

In an example, a syringe retaining wall 470 may be included on the plunger drive head 400 to help position and retain the plunger thumb flange on the drive head 400. Additionally, an outside wall 450 may be included on the plunger driver to protect the plunger during infusion. As illustrated in FIG. 4B, the drive head 400 also includes a plunger lever 409. The plunger lever 409 includes a thumb compression region, which provides an intuitive compression feature on the lever to assist user interaction. Actuation of plunger lever 409 opens plunger hooks 416, 417 (e.g., pivots hooks 416, 417 away from each other and syringe plane 460) allowing a user to position a syringe in pump 100. After releasing plunger lever 409, the plunger hooks pivot back towards syringe plane 460 and hold the plunger stem and thumb flange of the syringe.

Actuation of the plunger lever 409 may also move plunger hooks 416, 417 out from the drive head 400 towards the syringe barrel to provide additional space between plunger hooks 416, 417 and the pushing face of the drive head 400. The plunger hooks 416, 417 may be spring biased toward the pushing face of the drive head 400 to accommodate a wide variety of plunger flange thicknesses. The bias towards the drive head 400 and the syringe plane enable the plunger hooks 416, 417 to self-adjust to the size of plunger mounted in the pump.

In an example, the plunger hooks 416, 417 are spring loaded and biased inward to provide a substantial clamping force against the stem of the plunger as well as a compressive force that holds the plunger thumb flange against the drive head 400. The plunger hooks 416, 417 may first pivotally close before moving laterally towards the drive head 400 and returning toward their lateral home position. This sequence of closing motions ensures that the plunger stem is first centered by the arms, and then plunger thumb flange is brought into contact with the pushing surface.

Figure 4C:
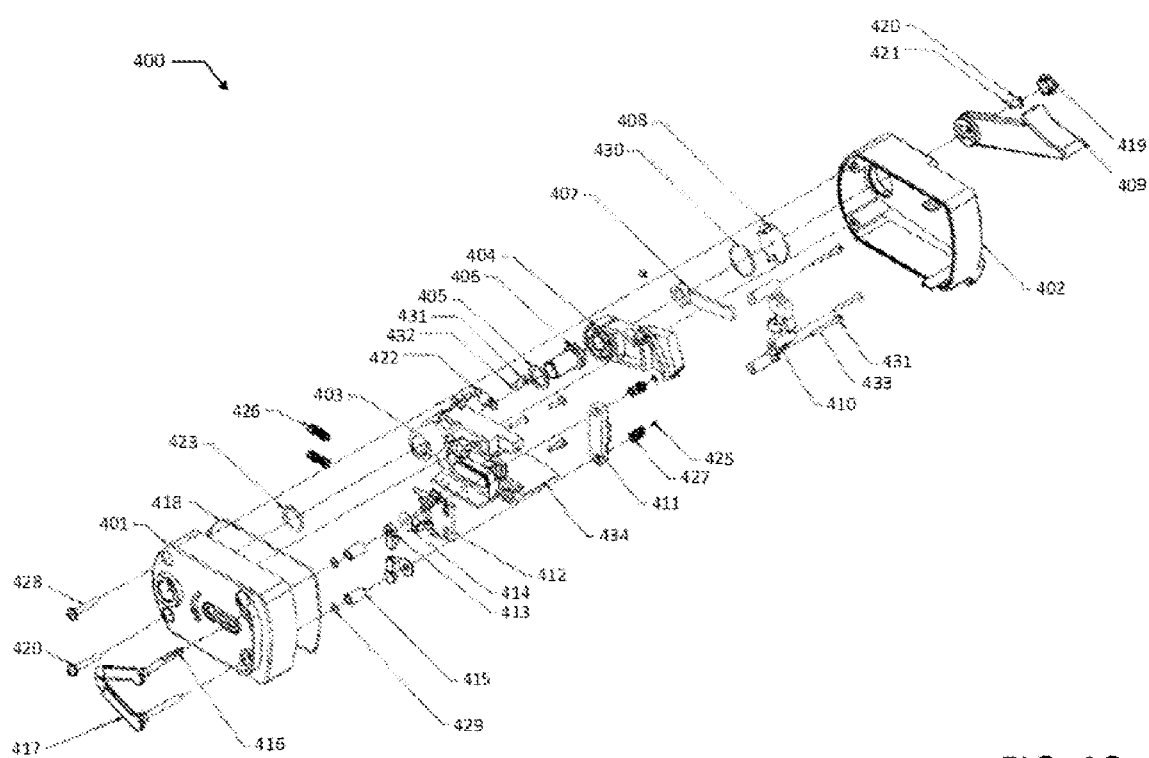
FIG. 4C is an exploded isometric view of a drive head of a syringe pump according to an example embodiment of the present disclosure.

FIG. 4C illustrates an exploded view of drive head 400. The drive head 400 may include a housing having a front case 401 and a rear case 402, which may have a gasketed interface (e.g., gasket 418) therebetween. Front case 401 and rear case 402 may be coupled together via a snap-fit connection and may be secured via screws 428 with optional washers 420. The plunger lever 409 may be positioned on the rear case 402 and coupled via lever clasp 419, screw 421 and/or washer 420. The plunger lever 409 is operatively coupled to the drive rod 132 via a plunger lever coupling 408, lever spring 422, clutch link 407, plunger hook lever 404 and plunger fix screw 406, which extends through the plunger base sensor assembly 403. The connections may also include an O-ring 430, washer 405 and O-ring 423.

Plunger hooks 416 and 417 are positioned on the front case 401 and extend through the housing and interface with hook slide plate 411, hook opener holder assembly 410 and hook opening plate assembly 412. The hook opening plate assembly 412 may include hook-opening springs 426 and may be coupled to a plunger hook sensor PCB which may include an SMT switch. The plunger hook sensor PCB may be mounted to the hook opening plate assembly 412 and the plunger base sensor assembly 403 via screws spaced by washers. The various mounting components for the plunger hooks 416 and 417 may include screws 433, washers 431, e-rings 421, springs 427, hook cover washers 414, hook links 413, plunger hook bushings 415, and plunger hook shaft O-rings 429.

The housing may house a plunger base sensor assembly 403 attached via washers and screws 432. The plunger base sensor assembly 403 may also include an insulation sheet 434. The plunger base sensor assembly 403 includes a plunger button that is held against a flat plastic plate within the plunger base sensor assembly 403, which directly contacts a cantilever beam inside the plunger drive head 400. The cantilever beam may include a strain gauge to measure the force acting on the plunger button.

Rotation of the plunger lever 409 is directly translated to "in and out" movement of plunger hooks 416, 417. A wiper lever attached in the hook opener holder assembly 410 may compress the hook slide plate 411 to create the "in and out" movement of plunger hooks 416, 417. As the plunger hook lever 404 pushes and rotates the small wiper lever, the wiper's wedge feature interacts with a roller within the hook slide plate 411. The hook slide plate 411 is controlled by compressing springs or hook holding springs 427. As the roller tracks down the wedge, the springs 427 are compressed and the plunger hooks 416, 417 are pushed away from the front case 401.

Rotation of the plunger lever 409 is also directly translated to rotation of plunger hooks 416, 417 via the plunger lever coupling 408. For example, the plunger hook lever 404 and the plunger lever 409 are held in the upward rest position by an extension spring or lever spring 422. The lever spring 422 is stretched as the plunger lever 409 is compressed and then returns the system to the rest position or "lever up" position when the plunger lever 409 is released. Specifically, the plunger hook lever 404 interacts with a second roller, attached on the hook opening plate assembly 412 that follows a track within the plunger hook lever 404. As the roller follows the track, the entire hook opening plate assembly 412 compresses the hook opening springs 426 to move linearly. The plate within the hook opening plate assembly 412 may include two identical slots that fit within the hook link and create rotational movement. The hook links securely connect to the plunger hook upper assembly shafts, so the rotational motion created moves the plunger hooks 416, 417 open. When the user releases the plunger lever 409, the hook opening springs 426 return the hook opening plate assembly 412 back to its original position, which rotates the plunger hooks 416, 417 back to the closed position.

As discussed above, the plunger hooks 416, 417 allow full compression of the syringe plunger and avoid interference with flange plate 160 thereby allowing the syringe pump 100 to more fully expel fluid from the syringe. For example, if the plunger hooks 416, 417 were alternatively positioned in a mirrored orientation that pivoted on an opposite side of the housing (e.g., closer to drive rod 132), the hooks may interfere with flange plate 160 preventing the syringe from fully compressing.

Each of the syringe loading components (e.g., barrel clamp, flange plate, flippers or plunger hooks) are adapted to capture and secure (e.g., load) a syringe in a manner that prevents an unintended bolus due to a syringe drive head impact. Discussed in more detail below, when a syringe 110 is loaded horizontally with the barrel flush against the barrel support face or rear wall 114, the barrel flange in the flange groove provided by the flange plate 160, the barrel clamp 150 pushing flush against the syringe barrel and the plunger thumb button within the plunger hooks 416, 417, the pump 100 may detect the barrel flange presence, the plunger button presence, and may also be able to identify syringe barrel outside diameter dimensions.

Syringe Pump Sensors

Syringe pump 100 includes various sensors to ensure proper operation and syringe loading. For example, pump 100 may include a clutch sensor, an occlusion sensor, a flange detection sensor, a barrel size sensor (e.g., barrel size measurement sensor), a syringe plunger position sensor, and a motor encoder. The flange detection sensor, barrel size sensor, and syringe plunger position sensor may work in conjunction as a syringe sensor system.

Figure 3A:
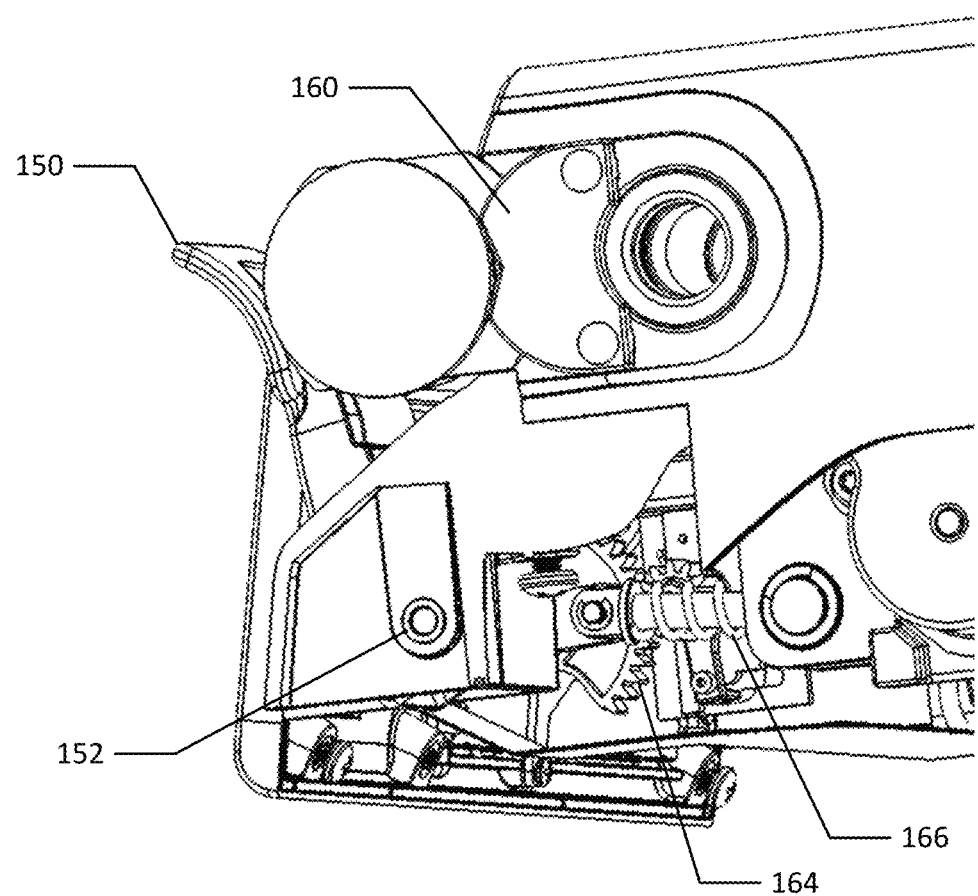
FIGS. 3A and 3B are partial views of a flange plate of a syringe pump according to an example embodiment of the present disclosure.
Figure 3B:
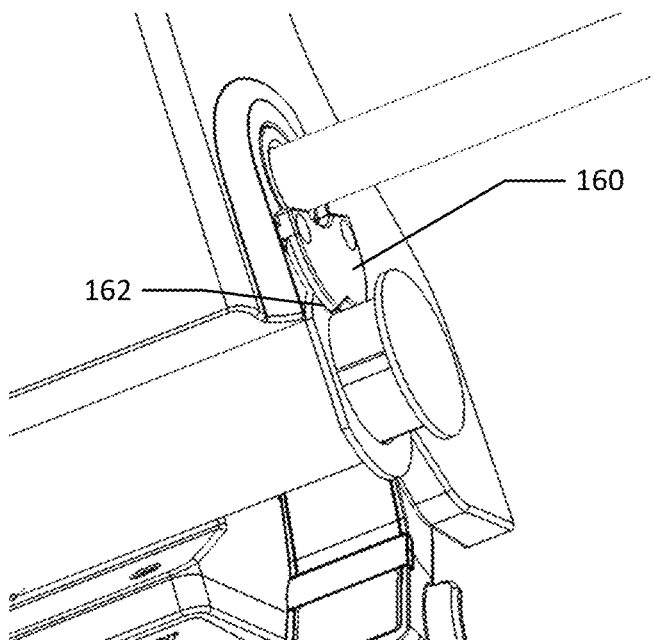

As discussed above, syringe barrel loading includes barrel size detection means, such as a barrel size sensor. For example, a rotary potentiometer may be used to detect the size of a syringe barrel. In another example, a linear potentiometer may be used to detect the size of the syringe barrel. As illustrated in FIG. 3A, rotation of the syringe barrel clamp 150 may be detected based on an amount of rotation or travel of gears 164 and/or compression of spring 166.

The sensors may track plunger position. For example, the plunger position sensor may include a linear pot wiper blade that is connected to the clutch and travels parallel with the lead screw. The sensor's resistance in circuit changes directly with the travel and outputs the voltage as a function of linear position. In another example, the syringe plunger position sensor may be an electromagnetic sensor that includes a magnet and a plunger linear sensor array.

The output from the plunger position sensor may be used to track the position of the syringe plunger. For example, tracked movements may be used to check if the plunger movement matches programmed delivery rate. The plunger position sensor may be used to check a Volume to Be Infused ("VTBI") command with the available volume in the syringe. For example, the syringe plunger position may be used to determine the remaining length of the barrel, which along with the barrel diameter may be used to determine the remaining volume in the syringe. The plunger position sensor may also be used to detect if a syringe has emptied or if an empty syringe has been loaded (e.g., detects a fully dispensed plunger position). Additionally, the plunger position sensor may be used to detect max deadstop (REOT, FEOT) position of the plunger head as well as to detect slope between the motor and clutch.

The sensors may indicate syringe size. The syringe barrel size sensor may include a linear pot wiper blade connected to the shaft of the barrel clamp 150. The sensor resistance in the circuit changes directly proportional to the travel of the barrel clamp 150 and outputs the voltage as a function of position. In another example, the syringe barrel size sensor may be an electromagnetic sensor that includes a magnet and a barrel linear sensor array. The magnet is mounted on the syringe barrel clamp assembly. The linear sensor array is mounted generally adjacent thereto and has a sensor. Because the movement of the syringe barrel clamp is less than the plunger movement, a single sensor can be used. Similar to the syringe plunger position sensor, based on the signal levels sensed by the sensor, the sensor can determine what size syringe is loaded into the pump.

The syringe barrel size sensor may be used to indicate if an incompatible syringe is loaded in pump 100. Additionally, the sensor may be used as a gross indication that a tube is not closed properly.

The flange detection sensor may be a micro switch that is located behind the barrel flange retention plate. In an example, the switch is depressed by the plate when the syringe flange is pushed into place during syringe loading. The flange detection sensor may indicate that the barrel is in its proper position and may be used to initiate pump power-up.

A plunger button detect sensor positioned on the drive head 400 detects the presence of a syringe. For example, a micro switch may be located in the plunger drive head 400 such that the switch is depressed by the plunger flange when the syringe flippers or plunger hooks 416, 417 capture the plunger flange during syringe loading. The plunger button detect sensor indicates presence of the plunger flange at the drive head 400 to verify the syringe is properly loaded.

A syringe force sensor or down stream occlusion ("DSO") sensor may be located on the drive head and may be used to indicate force or pressure on the syringe plunger. The calculated pressure may be used to determine a downstream occlusion, discussed in more detail below. Additionally, the force sensor may be used to perform start-up compensation to determine when the slack in syringe travel is removed. The syringe force sensor may also be used to detect a fully spent syringe as well as to detect the plunger flange.

The pump sub-assembly, as previously described, has associated therewith a plurality of sensors, which are operative to provide information as to the function and location of the various elements thereof. A clutch sensor may comprise an optical switch with a mechanical shutter that moves to block light. The clutch sensor may indicate that the clutch is engaged or disengaged.

A motor position sensor may comprise a rotary magnetic encoder. For example, a magnet may be mounted on the motor shaft, which turns with the motor and actives the rotary encoder count, which indicates the position of the motor (e.g., 15 revolutions per 1 revolution of leadscrew per 1 mm linear travel of plunger). In another example, the pump may include a drive motor shaft encoder comprising an encoder flag wheel attached to the armature shaft of the motor. The pump motor flag wheel may include a plurality of flags (e.g., twelve flags) extending radially outward from the hub thereof. The motor position sensor may indicate rotation of the motor and may be used to detect motor stall.

One or more of the above sensors (e.g., plunger position sensor) may be used to compensate for system slack during infusion startup.

Drive Mechanism

Figure 5A:
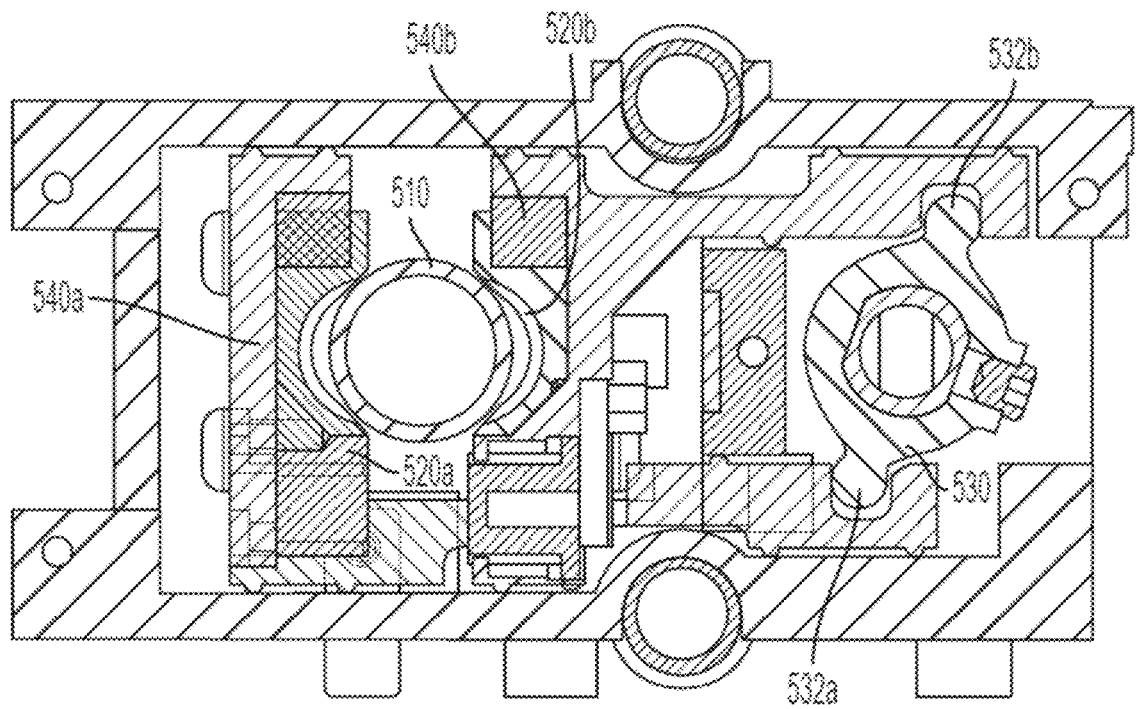
FIGS. 5A and 5B are views of drive mechanism components of a syringe pump according to an example embodiment of the present disclosure.

The syringe drive mechanism is accommodated by the pump housing and generally includes a motor, a lead screw 510, a split-nut (with nut halves 520a and 520b) and a slide assembly, and a drive head 400. As illustrated in FIG. 5A, the split-nut 520 is in an unengaged state (e.g., not contacting lead screw 510) and in FIG. 5B, the split-nut 520 is in an engaged state (e.g., contacting lead screw 510). The slide assembly is associated with the lead screw 510 and moves linearly in response to rotation of the lead screw 510 by the motor. Linear movement of the slide assembly and drive head 400 moves the syringe plunger, having a plunger flange, a plunger arm and plunger stopper, within the syringe barrel to expel fluid from the syringe assembly.

The motor is operably connected to the lead screw 510 to rotate the lead screw when the motor is energized. The lead screw 510 has threads that cooperate with a threaded member, such as a split-nut 520 of the slide assembly as will be described in greater detail below.

Typical half-nut designs may include a clutch mechanism with a half-nut that is spring biased against the lead screw. However, the spring bias may lead to additional stress levels on the half-nut, which may ultimately lead to thread wear on the half-nut. The additional stress and wear may also contribute to periodic fluctuations within a lead screw rotation cycle. Additionally, during an occlusion, half-nut drive mechanisms may experience stress levels that exceed the half-nut's yield strength, which over time may lead to half-nut failure (e.g., the threads of the half-nut may be significantly to completely worn away leading to pump failure). The half-nut wear may release an abrasion powder, for example material from worn half-nut threads, which may interfere with other pump components.

The improved split-nut 520 disclosed herein provides over twice as much thread engagement/contact than with traditional half-nut designs. Additionally, the split-nut 520 allows threads of the nut to be more concentric, which helps lower the flow rate accuracy ("FRA") periodic fluctuations and wear. For example, small movements of a half nut may create large variations of flow rate accuracy when threads are angled. Additionally, the halves 520a, 520b contact each other such that they are not biased against the lead screw 510, which advantageously lowers friction and wear and also increases reliability.

An example lead screw material is SUM24L (Electroless Nickel Plating). An example split-nut material is C95400 Aluminum Bronze. The materials listed for the lead screw and split-nut are not intended to be limiting and are provided as an example. Any other suitable material may be used.

The split-nut 520 of the slide assembly can be disengaged from the lead screw 510 allowing the slide assembly to freely slide along the lead screw 510 to linearly position the plunger drive head 400 against the plunger extending from the syringe barrel.

The nuts halves 520a, 520b are biased into engagement with the lead screw 510 by a spring and magnetic clutch. The threads on each of the nut halves 520a, 520b engage generally opposed sides of the lead screw 510. The split-nut configuration and anti-ratcheting clutch design maximizes performance and minimizes wear of the threads of the split-nut 520 and lead screw 510. With the threads engaged, when the motor rotates the lead screw 510, the split-nut 520 moves along the lead screw 510, which, in turn, linearly moves the drive head 400. This pushes the plunger into the syringe barrel to displace medicament from the syringe assembly.

Figure 5B:
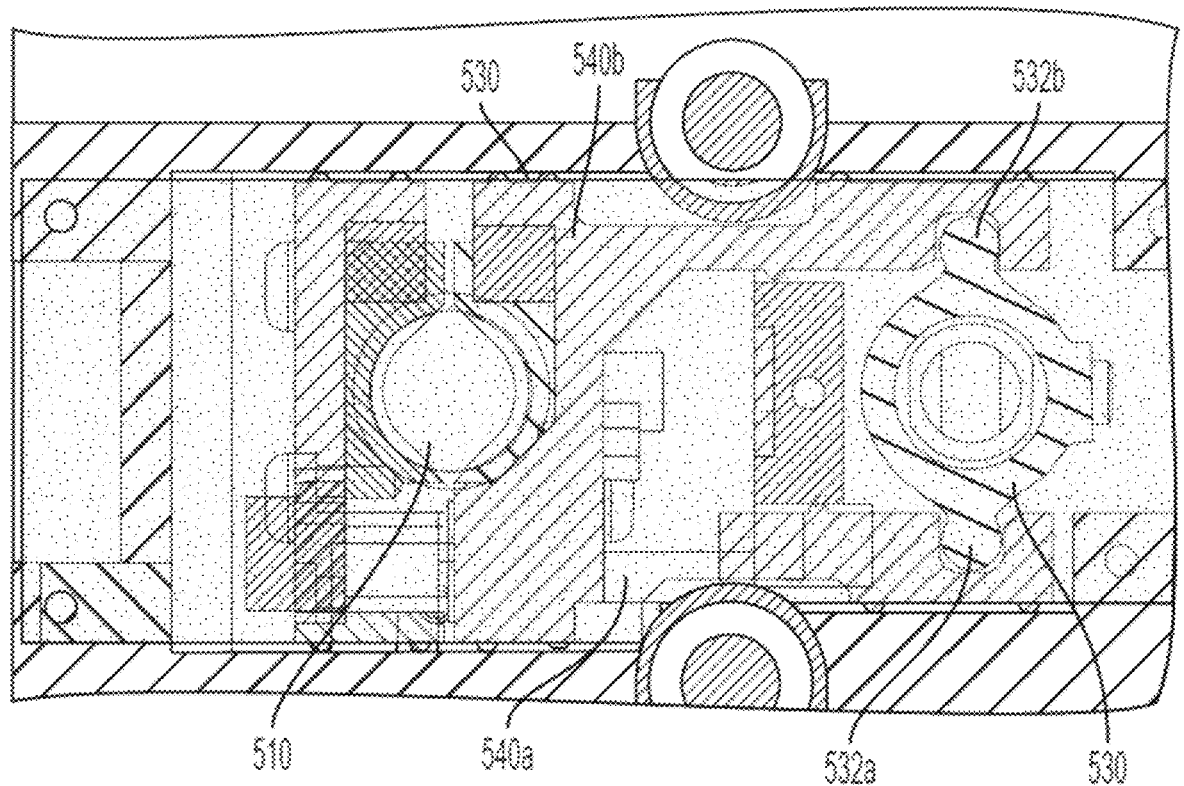

As mentioned above, the split-nut 520 can also be easily disengaged from the lead screw 510 which allows the slide assembly to be positioned along the lead screw 510 such as when positioning the drive head 400 against the syringe plunger. As illustrated in FIGS. 5A and 5B, a toggle 530 may rotate to move a first frame or clutch member 540a and a second frame or clutch member 540b. For example, key 532a may engage a corresponding groove in clutch member 540a and key 532b may engage a corresponding groove in clutch member 540b. As the toggle 530 rotates counter clockwise (from 5A to 5B), the frame or clutch members 540a, 540b are simultaneously drawn towards lead screw 510. For example, the toggle 530 pulls clutch member 540a towards lead screw 510 and pushes clutch member 540b towards lead screw 510. As shown in FIG. 5B, when the toggle 530 is in a vertical orientation, the split-nut 520 is fully engaged with lead screw 510. To disengage the split-nut 520 from the lead screw, toggle 530 may be rotated clockwise to push clutch member 540a away from lead screw 510 and pull clutch member 540b away from lead screw 510.

FIGS. 6A, 6B, 6C, 6D, 6E, 6F and 6G show various arrangements and mechanisms for disengaging the split-nut 520 from the lead screw 510. In the example illustrated in FIG. 6A, a camming action along with a spring that engage frames or clutch members associated with each nut half 520a, 520b to pull the split-nut 520 apart such that it disengages the lead screw 510. For example, a keyed cam 630 may rotate (e.g., clockwise) to engage and disengage split nut 520 from lead screw 510. As the keyed cam 630 rotates, the lobes interact with first and second frame or clutch members 640a, 640b. The first and second frame or clutch members may provide additional stiffness to the arrangement as the components (e.g., keyed cam 630 and spring 650) move in relation to the lead screw 510. When the lobes are fully engaged with each clutch member, the split-nut 520 is in a disengaged position where clutch member 640a is pushed away from lead screw 510 while clutch member 640b is pulled always from lead screw 510. As illustrated in in FIG. 6A, each clutch member 640a, 640b may be operatively coupled to an elastomeric member, such as a spring 650. As the cam lobes engage clutch members, spring 650 is compressed due to a pulling force from clutch member 640b and a pulling force from clutch member 640a, the which causes split-nut 520 to separate and disengage lead screw 510.

Once the split-nut 520 is disengaged from the lead screw 510, the slide member can move freely along the lead screw 510 to position the drive head 400.

Figure 6A:
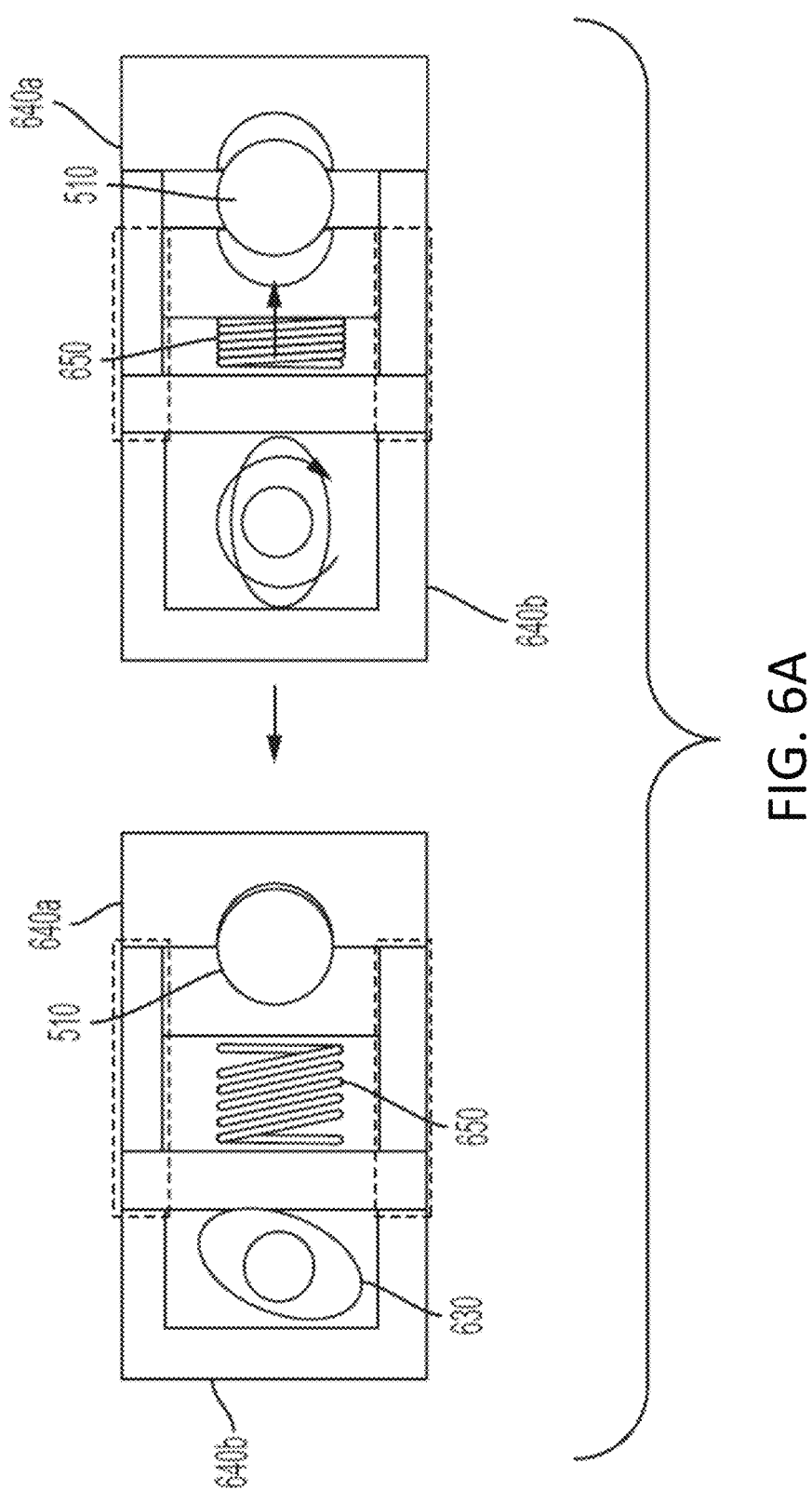
FIGS. 6A, 6B, 6C, 6D, 6E, 6F and 6G are views of various split-nut engagement mechanisms according to example embodiments of the present disclosure.
Figure 6B:
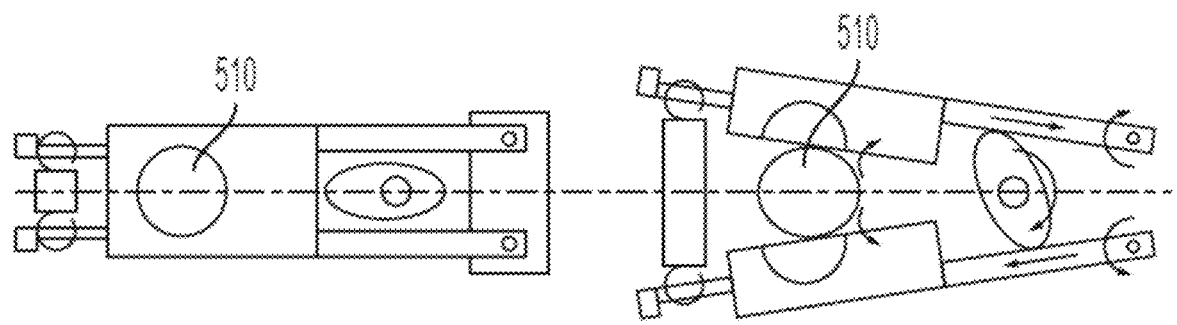
Figure 6C:
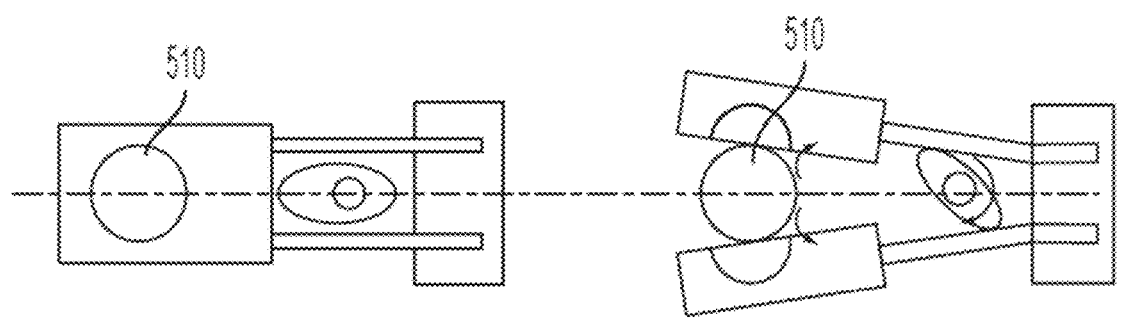
Figure 6D:
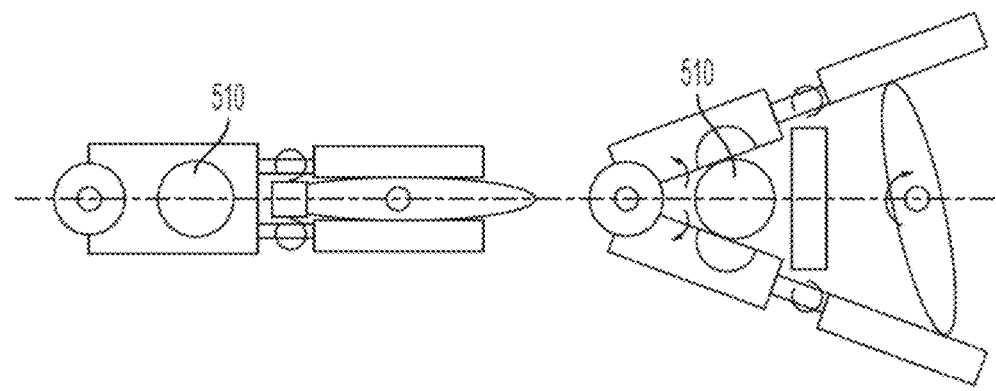
Figure 6E:
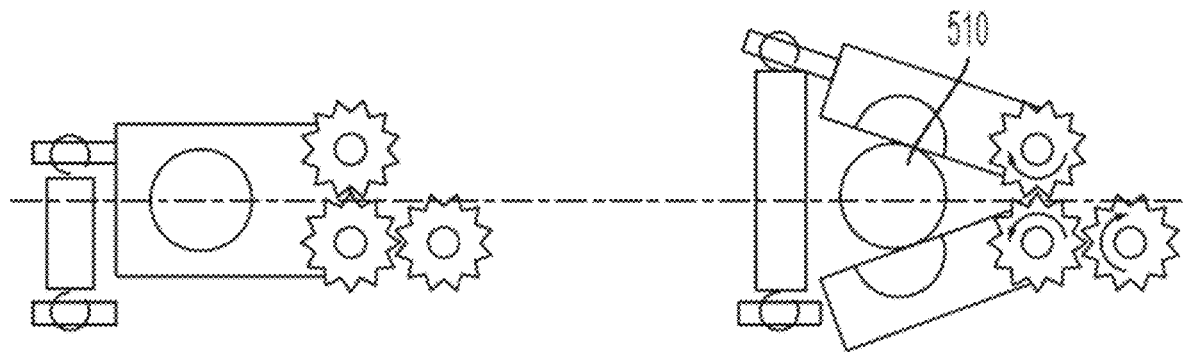
Figure 6F:
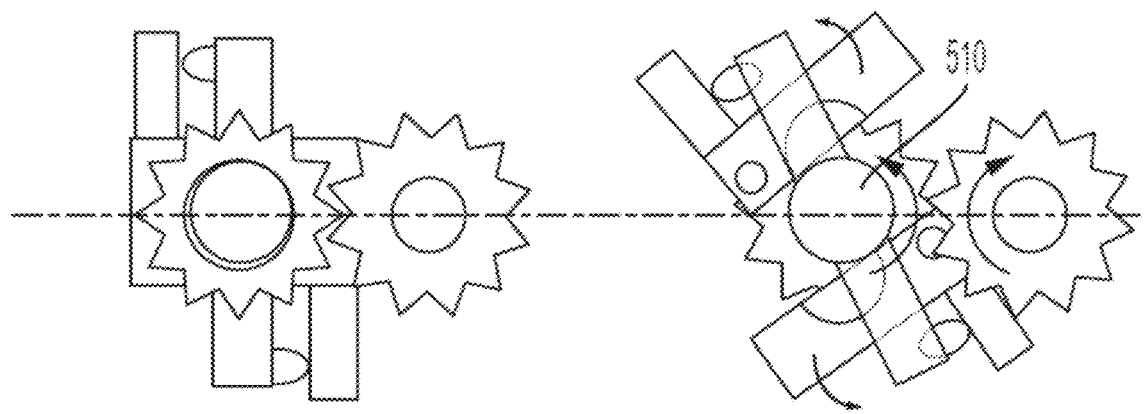
Figure 6G:
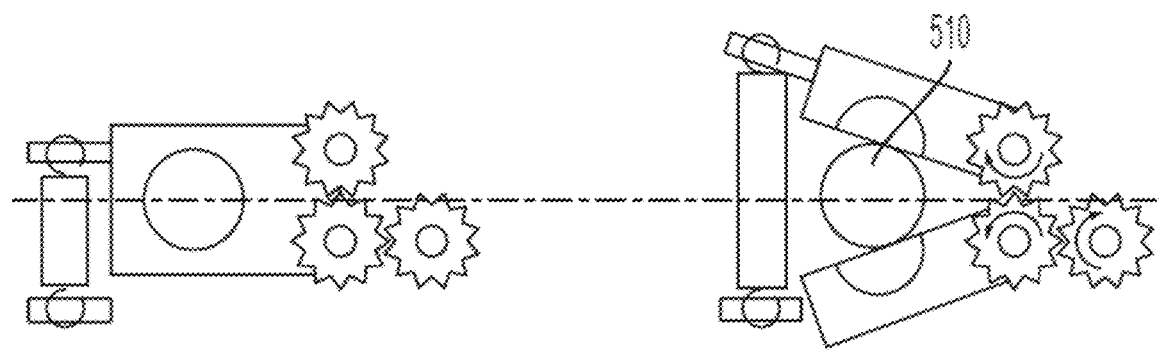

FIGS. 6B, 6C and 6D illustrate additional examples with a cam where the camming action rotates each nut half 520a, 520b about one or more pivot points such that the threads become disengaged from the threads on the lead screw 510. FIGS. 6E, 6F and 6G illustrate additional examples with gears that are rotated such that each nut half 520a, 520b is disengaged from the threads of the lead screw 510. In FIGS. 6E and 6G, a gear may be fixed to each half nut.

Anti-Ratcheting Magnetic Clutch

User actuation of the plunger lever 409 on the drive head 400 may also cause premature wear of the lead screw 510 used with a half-nut. For example, partial lever rotation with a half-nut allows the half-nut to remain in a partially engaged state. In this partially engaged state, a user can move the clutch and drag the half-nut threads across the lead screw threads (e.g., ratcheting). This ratcheting may cause premature wear of the threads and poor perception of quality.

Figure 5C:
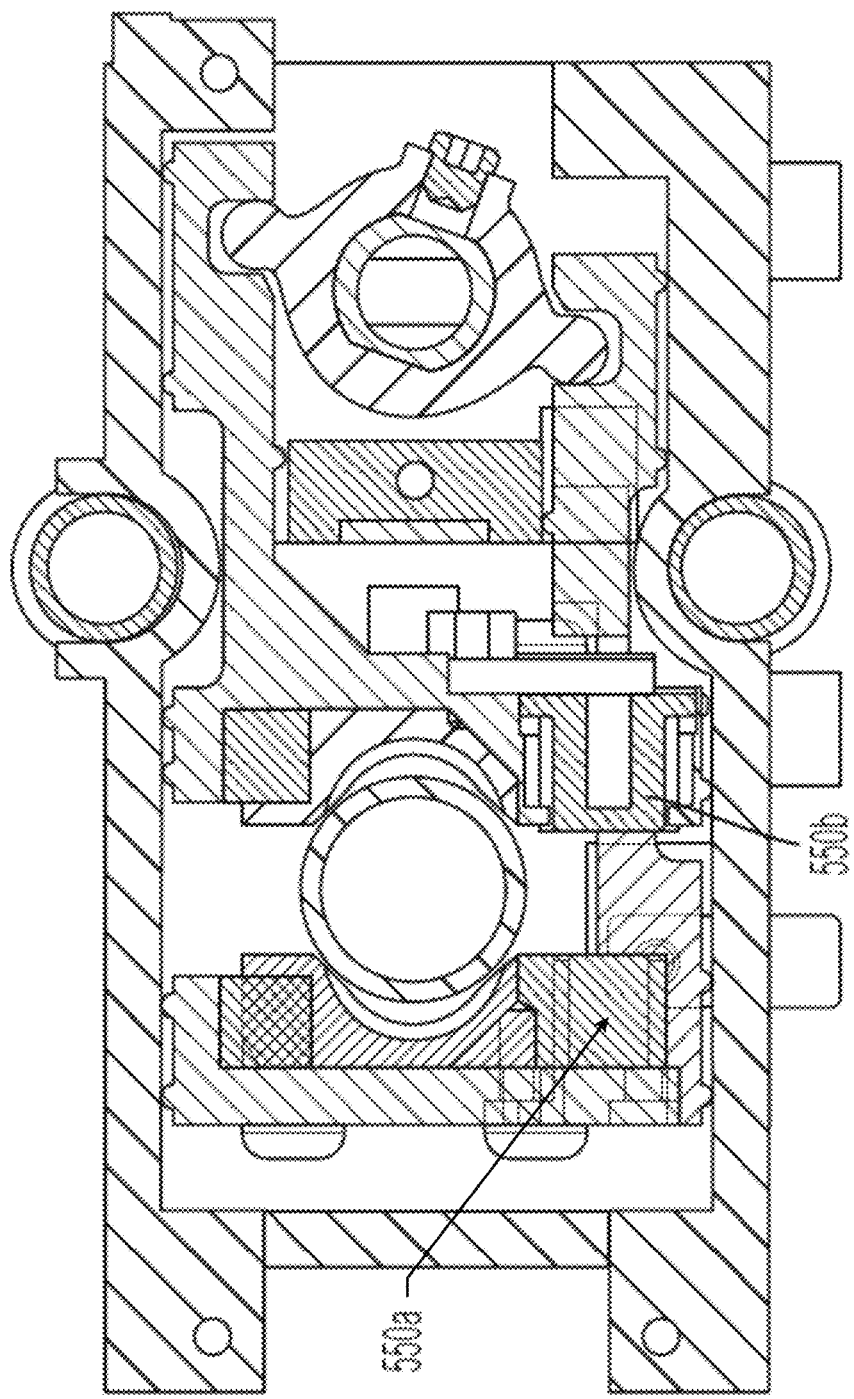
FIG. 5C is a partial view of a magnetic clutch assembly according to an example embodiment of the present disclosure.

Incorporating a magnet within the clutch to prevent the split-nut 520 from riding on the lead screw 510 improves reliability and prevents misuse. The magnet advantageously holds the clutch closed to provide additional security against unintended bolus. Additionally, in instances where ratcheting may typically occur, the magnetic force takes over and completely engages the split-nut 520 and therefore also requires or encourages a user to fully disengage the split-nut 520 to maintain the split-nut 520 in a disengaged position while manually moving the drive head 400. For example, magnetic members 550*a*, 550*b* are illustrated in FIG. 5C as an example position of magnets in the magnetic clutch.

For example, as illustrated in FIGS. 6A to 6G a magnet and/or spring may be implemented to provide an additional closing force to each of the nut halves 520*a*, 520*b*. Additionally, the greater closing and retention force requires a user to use a higher activation force when activating plunger lever 409, which results in the user fully opening or fully closing the clutch and preventing ratcheting and wear. In an example, additional magnets or spring bias may be positioned within the pump 100 such that a fully open clutch remains open until closed by the user.

Occlusion Detection

The pump may be equipped with an occlusion sensor to determine if an infusion line connected to the syringe barrel is blocked. In an example embodiment, the occlusion sensor is incorporated into the drive head of the drive mechanism. A force or pressure sensor in the drive head may measure a reactive force from the force pushing against the sensor. If too much force is required to move the plunger, it signifies that the infusion line is blocked. In another example, occlusions may be detected from clutch sensors and/or plunger position sensors.

Occlusions may be detected by monitoring force and/or pressure measurements using various techniques. Additionally, the user may select between rapid occlusion detection and non-rapid occlusion detection. In rapid occlusion detection mode, the syringe pump 100 may report an occlusion at 50% of the force or pressure thresholds discussed below.

Difference Value from Baseline

A baseline force value (e.g., a moving or sliding average window of force measurement samples, such as twenty samples) may be taken after the motor starts. The force and/or pressure sensor may output an Analog to Digital Converter ("ADC") count. In an example, the baseline force value may be a window of 20 samples of ADC counts after the pump motor starts. The current force measurement may be monitored and a difference value (e.g., baseline force value subtracted from the current value) may be determined. If the difference value exceeds a predetermined threshold, an occlusion alarm may sound. The pump may have various settings for various occlusion detection sensitivities (e.g., Very High, High, Medium High, Medium, Low, and Very Low). In a non-limiting example, the pump 100 may generate an alarm signal when the IV line pressure reaches 2 to 4 psi for a low sensitivity alarm, 6 to 9 psi for a medium sensitivity alarm, and 14 to 16 psi for a high sensitivity alarm.

In an example, the syringe pump 100 may generate a high priority downstream occlusion alarm for the following fluid pressures and sensitivities: (Sensitivity—Very High; Occlusion pressure 50 psi; Lower Limit 25 psi; Upper Limit 52 psi); (Sensitivity—High; Occlusion pressure 16 psi; Lower Limit 13 psi; Upper Limit 18 psi); (Sensitivity—Medium High; Occlusion pressure 13 psi; Lower Limit 10 psi; Upper Limit 15 psi); (Sensitivity—Medium; Occlusion pressure 10 psi; Lower Limit 7 psi; Upper Limit 12 psi); (Sensitivity—Low; Occlusion pressure 7 psi; Lower Limit 4 psi; Upper Limit 9 psi); and (Sensitivity—Very Low; Occlusion pressure 4 psi; Lower Limit 1 psi; Upper Limit 6 psi).

In another example, the syringe pump 100 may generate a high priority downstream occlusion alarm for the following fluid pressures and sensitivities: (Sensitivity—Very High; Occlusion pressure 50 psi; Limit <52 psi); (Sensitivity—High; Occlusion pressure 16 psi; Lower Limit 12 psi; Upper Limit 20 psi); (Sensitivity—Medium High; Occlusion pressure 13 psi; Lower Limit 10 psi; Upper Limit 15 psi); (Sensitivity—Medium; Occlusion pressure 10 psi; Lower Limit 7 psi; Upper Limit 12 psi); (Sensitivity—Low; Occlusion pressure 7 psi; Lower Limit 4 psi; Upper Limit 9 psi); and (Sensitivity—Very Low; Occlusion pressure 4 psi; Lower Limit 2 psi; Upper Limit 8 psi).

For the syringe pump 100, the syringe force contact is non-relaxing in nature and a change in temperature does not cause a material property change. Also, the force sensor for the syringe pump 100 is rated and compensated to operate from −10 degrees to 40 degrees C., which covers typical pump operating ranges without impacting system level temperature variations in DSO detection for the syringe. However, for an infusion pump, the tubing relaxes into the channel causing a change in force which is dependent on temperature. For example, the tube material properties change based on temperature and a temperature compensation slope may be added for both the baseline force value as well as current ADC values.

After the pump reaches steady state, occlusion detection may be based on a change in pressure or delta pressure instead of the High, Medium, or Low threshold settings. For example, after reaching steady state where the pressure is very steady, a sudden shift upwards for pressure may indicate that the pump is trending to occlusion. Monitoring a delta pressure after steady state may allow for earlier occlusion detection.

In an example, steady state is achieved when there is less than a 1 psi pressure change in the last two minutes of pressure measurements. If the system is not in a steady state condition, pressure delta sensing may be disabled.

The pump may also monitor changes in pressure as a function of flow rate. Different baseline and/or different threshold levels may be established based on the flow rate. For example, if the difference in pressure from baseline exceeds a predetermined relationship (e.g., pressure Increase=0.3*Flowrate in a 1 minute duration), an alert or warning for an occlusion sounds.

As discussed above, a syringe force sensor or down stream occlusion ("DSO") sensor may be located on the drive head and may be used to indicate force or pressure on the syringe plunger. The calculated pressure may be used to determine a downstream occlusion. In another example, upon starting an infusion, the pump may record an initial baseline measurement during a first start-up interval (e.g., during the first ten seconds). At the beginning of the first start-up interval (e.g., over the first second of the ten second interval), the pump may record the initial baseline measurement via a moving average of ADC counts. The baseline measurement may be updated to a lower filtered ADC value recorded within the first start-up interval. For example, if a filtered ADC value recorded at four seconds is lower than the initial baseline measurement recorded at one second, the filtered ADC value recorded at four seconds may replace the initial baseline measurement recorded at one second.

The pump may continuously compute the pressure in real time as ADC values are monitored during the infusion. For example, the pump may continually compute the Syringe DSO Pressure according to the below equation. The Calibration Factor may be based on the syringe size and may be stored in a database that has different values for different syringe sizes.

$$\text{Syringe } DSO \text{ Pressure} = \frac{(\text{Current Filtered } ADC - \text{Current Filtered Baseline})}{\text{Calibration Factor}}$$

During the first start-up interval, occlusion detection may be based on syringe size. With syringe sizes lower than a predetermined size (e.g., 6 ml or less, 10 ml or less, etc.), occlusion detection may be determined by a dual criteria of curvature and drop. For example, an occlusion may be reported during the first start-up interval if a DSO threshold is exceeded for a threshold period (e.g., three seconds) by a plurality of filtered samples within the threshold period. Specifically, the ADC value may be monitored and a difference value (e.g., baseline value subtracted from the current ADC value) may be determined. If the difference value exceeds the DSO threshold, an occlusion alarm may sound. The quantity of samples may be predetermined and in some examples may include all filtered samples within the threshold period.

Conversely, for syringes larger than the predetermined size (e.g., 6 ml or larger, 10 ml or larger, etc.), an occlusion may be reported when a filtered sample exceeds the DSO threshold. In this example, an occlusion may be reported when any filtered sample exceeds the DSO threshold.

During a second start-up interval (e.g., during the first thirty seconds), for a rapid mode infusion, an occlusion alarm may sound (when the non-rapid occlusion detection mode is selected) when the occlusion pressure threshold is exceeded. In rapid infusion, the syringe pump (e.g., GUI) may calculate both the non-rapid and rapid threshold levels and report both to the syringe pump (e.g., pumphead manager). The syringe pump 100 may select the non-rapid threshold for the second start-up interval and then may report occlusions using the rapid threshold after the second start-up interval.

After the first and second start-up intervals, a new baseline measurement may be acquired by searching for a baseline window (e.g., a five second window, ten second window, etc.) where the ADC samples within the baseline window are within a predetermined ADC value range (e.g., +/−50 ADC counts). In another example, the baseline window may be established based on a predetermined psi value range (e.g., +/−2 psi). In another example, the baseline window may be established based on a combination of a predetermined ADC value range and a predetermined psi value range, such as based on either the predetermined ADC value range or the predetermined psi value range, whichever is smaller (e.g., +/−50 ADC counts or +/−2 psi). Additionally, when establishing the baseline window, the psi value may have an upper limit (e.g., no greater than 3.87 psi above the current baseline measurement). Establishing a new baseline measurement may be performed once or multiple times for each infusion start. For example, the above processes may be a one-time baseline correction per infusion start. As previously mentioned, the baseline measurement may be updated to a filtered ADC value that is lower than the current established baseline.

Additionally, after the first and second start-up intervals, an occlusion may be reported when a filtered sample exceeds the DSO threshold. For example, an occlusion may be detected and reported as the threshold is crossed. As discussed above, the ADC value may be monitored and a difference value (e.g., baseline value subtracted from the current ADC value) may be determined. If the difference value exceeds the DSO threshold, an occlusion alarm may sound. Additionally, the current force measurement may be monitored by the pump and a difference value (e.g., baseline force value subtracted from the current value) may be determined. If the difference value exceeds a predetermined threshold, an occlusion alarm may sound. If rapid occlusion detection mode is selected, the syringe pump 100 may report an occlusion at 50% of the force or pressure thresholds discussed above. Rapid occlusion detection mode may be limited to lower flow rates (e.g., approximately 20 ml/hr. or less) because if the pump is performing a rapid infusion with high flow rates, then occlusion detection may occur quicker as the pump is already utilizing a naturally high flow-rate.

Slope of Pressure Measurements

An occlusion alarm may be generated if the slope calculated from the difference of two pressure measurements exceeds a threshold value. The pressure measurements may be taken in a predetermined window or time interval, for example, every two seconds. In an example, two different slope measurements may be used to account for any braking forces at the start of an infusion. To prevent false alarms, the initial threshold value may be higher to account for braking forces from the tubing or other pump components at start-up. After start-up, the threshold value may be lower after the pump has overcome the braking forces.

Area Under Force Curve

Occlusion detection may also be based on energy spent or the area between a base line and the current force line. The pressure change and linear displacement (e.g., for a syringe pump) may also be used to determine whether an occlusion is present. In either of the above examples, the area calculation may be compared to a threshold value.

Accelerometer

Digital moving average filters filter out unwanted spikes and/or noise signals. However, mechanically generated noise may also be unexpected and irregular which may lead to false alarms. In some instances, the mechanically generated noise may be more problematic than electrical noise.

An accelerometer may be used to help distinguish and/or filter mechanically induced sudden noises and/or spikes. Example sources of such noise may be from an operator pushing on the door of the infusion pump, an operator bumping into the pump, an operator moving the pump and patient while infusing, etc.

If the pump drops from a height or a syringe pump syphons due to the impact to the plunger, a separate high priority alarm can be sent to the user. If the accelerometer picks up mechanical movement/vibrations due to door movement or key selection (e.g., pressing display or physical keys), a feedback signal is sent to pump to not alarm or auto-restart because the event was purely caused by a sudden mechanically induced spike. Consequently, following an impact/drop a separate diagnostic algorithm is run on the sensors to test the functionality of the sensors and/or other critical components. For example, the diagnostic algorithm may ensure that the impact or drop did not disable or impair any of the sensor functions to ensure that the pump can detect and filter future vibration or drop events. When there is no impact but sudden irregular pressure spike(s) are detected by the occlusion algorithm, it can be confirmed from the accelerometer that it was purely electrically induced. If these spikes are sudden and irregular and not within an expected occlusion spike range an electrically induced sensor failure alarm is generated.

With an accelerometer sensitive enough to detect smaller movements/vibrations, a tubing tug or pulled scenario is confirmed in addition to the force sensor signal characteristics.

Figure 7:
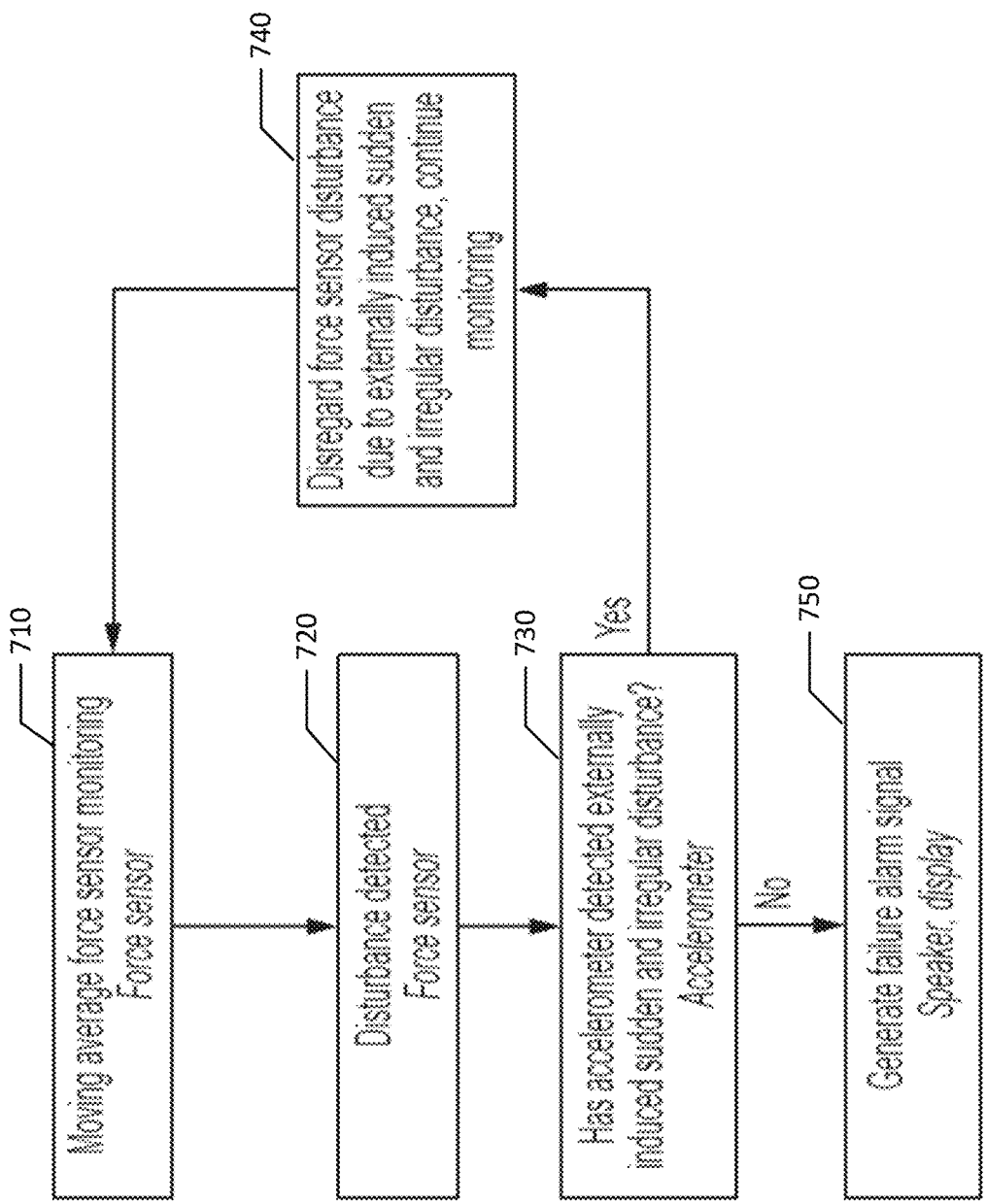
FIG. 7 is an example flow chart for detecting a disturbance of a pump using an accelerometer according to an example embodiment of the present disclosure.

As illustrated in FIG. 7, a moving average force sensor may monitor the forces applied to select locations on the pump (block 710). If a disturbance, or sudden pressure/force spike is detected (e.g., from the force sensor) (block 720), the system may check whether the accelerometer has detected an externally induced sudden or irregular disturbance (block 730). If the accelerometer has detected an externally induced and irregular disturbance, the pump may disregard the force sensor disturbance and continue monitoring (block 740). For example, the system may determine that the disturbance was due to an externally induced and irregular disturbance and disregard the disturbance to continue monitoring (e.g., at block 710) for internal (e.g., non-externally induced) disturbances. However, if the accelerometer has not detected an external event, the pump may generate a failure alarm signal to indicate that alarm condition (block 750), such as the presence of an occlusion. The pump may create an audible alarm through speakers or may indicate the alarm condition on the display.

Operational Indicators

LEDs may be placed on the pump 100 to indicate the pump is "ON" as well as flow direction. In some examples (e.g., with multi-colored LEDs such as tri-colored LEDs) the LEDs may be used to indicate some of the basic pump states when the display is off to reduce power consumption.

Operation of each of the above modes may be changed within the pump settings. Additionally, the display may depend on whether operation is from the power cord or battery. For example, to conserve the battery, the LED and other light indicators may be used. However, when operating via a power cord, both the LED/light indicators and the display may be used to provide visual indications and prompts to the user.

Rack Power Management

The infusion pump disclosed herein and/or a syringe pump may be used with a rack configured to house one or more pumps (e.g., infusion and/or syringe pumps). The rack may provide dynamic power and heat management for each pump housing within the rack. The power and heat management may be based on medication criticality that each respective pump is delivering. For example, a pump housed in the rack that is delivering a highly critical medication may be allocated more power so that the battery is charged to a level that reduces risk to the patient from a depleted battery after AC has been removed.

The rack may assist with pump identification, pump-to-pump communication, pump-to-rack and rack-to-pump communication, pump battery charging, etc. The rack may also manage power based on medication criticality and may also manage motor consumption per medication needs.

The rack may provide a common display and external connectivity via a wired or wireless connection.

The rack may implement several methods or procedures to control battery consumption and charging of the various infusion pumps and/or syringe pumps housed in the rack. The rack may allow a pump power supply or wall wart to draw higher current for faster charging. For example, the rack may allocate rack power to each pump such that its battery will be charged to a level that reduces risk to a patient from a depleted battery after AC-power has been removed. If a patient is receiving a critical medication along with a noncritical IV solution, the pump delivering the critical therapy may be given charging priority such that it is allowed to charge its battery faster than other pumps housed in the rack. The rack may also manage the amount of power that a pump is using for things other than battery charging, such as driving its motor. If one pump is using more power to drive its motor then that pump may be allowed to have a higher charge current so that when unplugged, the run time on the battery will be similar for all pumps housed in the rack. The rack may also prioritize and assign fast charging vs. trickle charging on a pump to pump basis based on criteria, such as charge need, medication being delivered, etc.

The rack may also detect failure modes, such as exceeding thermal constraints on power supplies.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention claimed is:

1. A syringe pump comprising:
    a housing with a syringe accepting region;
    a syringe holding system configured to hold a syringe in the syringe accepting region;
    a drive mechanism including:
        a lead screw,
        at least one half nut,
        an anti-ratcheting magnetic clutch assembly, and
        a drive rod, and
        wherein the anti-ratcheting magnetic clutch assembly is configured to engage and disengage the at least one half nut to and from the lead screw, and
        wherein the anti-ratcheting magnetic clutch assembly includes a spring and a magnetic clutch that are configured to bias the at least one half nut into engagement with the lead screw; and
    a drive head operatively coupled to the drive mechanism, the drive head configured to engage a piston of the syringe held by the syringe holding system,
    wherein the drive head includes a plunger lever disposed at a distal-most end of the drive head.

2. The syringe pump of claim 1, wherein the syringe accepting region includes a concave rear wall having a vertex, where the concave rear wall includes a top portion and a bottom portion that meet to form the vertex, and wherein the top portion is oriented at a first angle with respect to a vertical plane intersecting the vertex.

3. The syringe pump of claim 2, wherein the bottom portion is oriented at a second angle with respect to the vertical plane intersecting the vertex.

4. The syringe pump of claim 3, wherein the first angle and the second angle are the same.

5. The syringe pump of claim 1, wherein the drive head includes first and second plunger hooks disposed on the drive head and configured to grasp onto a plunger thumb flange of a plunger of the syringe, and wherein the first and second plunger hooks are configured to actuate between an open position and a closed position.

6. The syringe pump of claim 1, wherein the plunger lever is adapted to move first and second plunger hooks between an open position and a closed position, and wherein the plunger lever is configured for actuation by a user.

7. The syringe pump of claim 1, wherein the spring and the magnetic clutch are configured to increase a holding force of the anti-ratcheting magnetic clutch assembly and prevent ratcheting.

8. The syringe pump of claim 1, wherein the syringe holding system includes a barrel clamp, a flange plate, and first and second plunger hooks.

9. The syringe pump of claim 8, wherein the barrel clamp includes a proximal end pivotably attached to the housing and a distal end with a barrel engagement surface, wherein the barrel engagement surface is attached to the barrel clamp via a swivel and is adapted to allow the barrel engagement surface to rotate and contact syringe barrels of at least two different sizes.

10. The syringe pump of claim 8, wherein the flange plate is configured to secure a syringe barrel flange against the housing, the flange plate is biased towards the housing, the flange plate includes a bottom surface configured to contact the syringe barrel flange, and the flange plate has a surface profile that transitions from a flat surface to an angled surface towards an edge of the flange plate.

11. The syringe pump of claim 1, wherein the magnetic clutch includes two magnetic clutch members having opposite polarities, wherein the opposite polarities are configured to create a magnetic force which engages the at least one half nut to the lead screw.

12. The syringe pump of claim 1, further comprising an occlusion sensor, wherein the occlusion sensor is configured to communicate with a processor that determines if an infusion line connected to a syringe barrel is blocked.

13. The syringe pump of claim 12, wherein the occlusion sensor communicates with the processor to determine if the infusion line is connected to the syringe barrel is blocked by calculating one of a slope of a force curve, a slope of a pressure curve, a comparison to a baseline force measurement, a comparison to a baseline pressure measurement, or an area under the force curve.

14. The syringe pump of claim 1, further comprising an accelerometer, wherein the accelerometer is configured to communicate with a processor that detects at least one of an occlusion or whether the syringe pump experienced an external impact.

15. The syringe pump of claim 1, wherein the syringe pump is positioned in a rack with at least one other infusion pump or syringe pump.

* * * * *